(12) United States Patent
Volland et al.

(10) Patent No.: US 7,145,042 B2
(45) Date of Patent: *Dec. 5, 2006

(54) METHOD FOR PRODUCING DIALDEHYDES AND OR ETHYLENICALLY UNSATURATED MONOALDEHYDES BY HYDROFORMYLATING ETHYLENICALLY UNSATURATED COMPOUNDS

(75) Inventors: Martin Volland, Heidelberg (DE); Wolfgang Ahlers, Worms (DE); Klaus Ebel, Lampertheim (DE); Rocco Paciello, Bad Dürkheim (DE); Michael Röper, Wachenheim (DE); Thomas Mackewitz, Mannheim (DE); Volker Böhm, Schifferstadt (DE); Xavier Sava, Mannheim (DE); Oliver Löber, Freimersheim (DE); Oliver Bey, Niederkirchen (DE); Jürgen Stephan, Mannheim (DE); Frank Haese, Lambsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 10/527,635

(22) PCT Filed: Sep. 12, 2003

(86) PCT No.: PCT/EP03/10166

§ 371 (c)(1),
(2), (4) Date: Mar. 14, 2005

(87) PCT Pub. No.: WO2004/026803

PCT Pub. Date: Apr. 1, 2004

(65) Prior Publication Data

US 2006/0052645 A1   Mar. 9, 2006

(30) Foreign Application Priority Data

Sep. 13, 2002   (DE) ............................... 102 42 636

(51) Int. Cl.
*C07C 45/50* (2006.01)
(52) U.S. Cl. ....................... 568/451; 568/454
(58) Field of Classification Search ................ None
See application file for complete search history.

(56) References Cited

U.S. PATENT DOCUMENTS

| | | |
|---|---|---|
| 3,816,452 A | 6/1974 | Mrowea |
| 5,710,344 A | 1/1998 | Breikss et al. |
| 5,907,045 A | 5/1999 | Antognazza et al. |
| 6,852,661 B1 | 2/2005 | Ahlers et al. |
| 2003/0022947 A1 | 1/2003 | McAtee et al. |
| 2003/0055253 A1 | 3/2003 | Ahlers et al. |
| 2003/0195378 A1 | 10/2003 | Ahlers et al. |
| 2004/0110960 A1 | 6/2004 | Ahlers et al. |
| 2005/0020857 A1 | 1/2005 | Volland et al. |
| 2006/0052645 A1 | 3/2006 | Volland et al. |

FOREIGN PATENT DOCUMENTS

| | | |
|---|---|---|
| CA | 2 399 431 | 8/2001 |
| DE | 100 23 471 | 11/2001 |
| DE | 100 46 026 | 3/2002 |
| DE | 102 391 134 | 1/2003 |
| EP | 0 754 715 A2 | 1/1997 |
| JP | 2002-047294 | 2/2002 |
| WO | WO-95/30680 | 11/1995 |
| WO | WO-98/42716 | 10/1998 |
| WO | WO-99/52632 | 10/1999 |
| WO | WO-99/52915 | 10/1999 |
| WO | WO-00/56451 | 9/2000 |
| WO | WO-01/85739 | 1/2001 |
| WO | WO-01/58589 | 8/2001 |
| WO | WO-02/083695 | 10/2002 |
| WO | WO-03/018192 | 3/2003 |
| WO | WO-03/062251 | 7/2003 |
| WO | WO-03/066642 | 8/2003 |

OTHER PUBLICATIONS

Kranenburg, Mirko et al., "New Diphosphine Ligands Based on Heterocyclic Aromatics Inducing Very High Regioselectivity in Rhodium-Catalyzed Hydroformylation: Effect of the Bite Angle," Organometallics 1995, 14, pp. 3081-3089.
Trzeciak, A.M. et al., "1,5-Hexadiene Selective Hydroformylation Reaction Catalyzed With Rh(acac)(P(OPh)3 and Rh(acac)(CO)(PPh$_3$)/PPh$_3$ Complexes" Journal of Organometallic Chemistry, 464 (1994) pp. 107-111.
Botteghi, C. et al., "Preparation of Linear Long Chain Dialdehydes by Hydroformylation of Linear $\alpha$, $\omega$-dienes or $\omega$-vinylaldehyde Acetals," Journal of Molecular Catalysis A: Chemical 175 (2001) pp. 17-25.
van der Slot, Saskia et al. "Rhodium Complexes Based on Phosphorous Diamide Ligands: Catalyst Structure Versus Activity and Selectivity in the Hydroformylation of Alkenes," Organometallics 2000, 19, pp. 2504-2515.
Brunner et al., "Optisch aktive Aminosphosphane—Synthese und Verwendung in der Rh-katalysierten enantioselektiven Hydrosilylierung", Chem. Ber., vol. 118, pp. 3380-3395 (1985).

(Continued)

*Primary Examiner*—Sikarl A. Witherspoon
(74) *Attorney, Agent, or Firm*—Connolly, Bove, Lodge & Hutz, LLP

(57) ABSTRACT

The invention relates to a method for producing dialdehydes and/or ethylenically unsaturated monoaldehydes by reacting at least one compound with at least two ethylenically unsaturated double bonds with carbon monoxide and hydrogen in the presence of a hydroformylating catalyst with at least one complex of a metal of subgroup VIII. The subgroup comprises at least pnicogen chelate ligands.

12 Claims, 1 Drawing Sheet

OTHER PUBLICATIONS

Moloy et al., "N-Pyrrolyl phosphines: An Unexploited Class of Phosphine Ligands with Exceptional π-Acceptor Character", *J. Am. Chem. Soc.*, vol. 117, pp. 7696-7710 (1995).

Trzeciak et al., "Novel rhodium complexes with N-pyrrolylphosphines: attractive precursors of hydroformylation catalysts", *J. Chem. Soc., Dalton Trans.*, pp. 1831-1837 (1997).

Trzeciak et al., "Rhodium complexes $HRh[P(NC_4H_4)_3]_4$ and $HRh(CO)[P(NC_4H_4)_3]H_3$ as active catalysts of olefins and arenes hydrogenation X-ray structure of $HRh(CO)[P(NC_4H_4)_3]_3$", *Journal of Organometallic Chemistry*, vol. 552, pp. 159-164 (1998).

Shen et al., "Enthalpies of Reaction of $Cp'=C_5H_5$, $C_5Me_5$; COD= Cyclooctadiene) with π-Acceptor Chelating Phosphine Ligands", *Organometallics*, vol. 17, No. 14, pp. 3000-3005 (1998).

Gimbert et al., "Synthesis and Characterization of New Binuclear (Co)(0) Complexes with Diphosphinoamine Ligands. A Potential Approach for Asymmetric Pauson-Khand Reactions", *Journal Organometallic Chemistry*, vol. 64, pp. 3492-3497 (1999).

Trzeciak et al., "Novel rhodium(I) complexes with (2-hydroxyphenyl)diphenylphosphine ligand: catalytic properties and X-ray structures of $Rh(OC_6H_4PPh_2)(CO)PPh_3)$ and $Rh(OC_6H_4PPh_2)\{P(OPh)_3\}_2\cdot0.5C_6H_6$", *Journal of Organometallic Chemistry*, vol. 575, pp. 87-97 (1999).

Trzeciak et al., "Hydroformylatin of vinylsilanes with $Rh(acac)(CO)_2$/tris(N-pyrrolyl)phosphiine catalytic system", *C.R. Acad. Sci. Paris,* 1.2, Série II c, p. 235-239 (1999).

van der Veen et al., "New Phosphacyclic Diphosphines for Rhodium-Catalyzed Hydroformylation", *Organometallics*, vol. 18, pp. 4765-4777 (1999).

Smith, Jr. et al., "Synthetic, Structural, and Solution Calorimetric Studies of $Pt(CH_3)_2(PP)$ Complexes", *Organometallics*, vol. 19, pp. 1427-1433 (2000).

Benincori et al., "3,3'-Bis(diphenylphosphino)-1,1'-disubstituted-2,2'-biindoles: Easily Accessible, Electron-Rich, Chiral Diphosphine Ligands for Homogeneous Enantioselective Hydrogenation of Oxoesters", *J. Org. Chem.*, vol. 65, pp. 8340-5347 (2000).

Selent et al., "Neuartige oxyfunktionalisjerte Phosphonitliganden für die Hydroformylierung isomerer n-Olefine", *Angew. Chem.*, vol. 112, No. 9, pp. 1694-1696 (2000).

van der Slot et al., "Rhodium Complexes Based on Phosphorus Dlamide Ligands: Catalyst Structure versus Activity and Selectivity in the Hydroformylation of Alkenes", *Organometallics*, vol. 19, pp. 2504-2515 (2000).

METHOD FOR PRODUCING DIALDEHYDES AND OR ETHYLENICALLY UNSATURATED MONOALDEHYDES BY HYDROFORMYLATING ETHYLENICALLY UNSATURATED COMPOUNDS

RELATED APPLICATIONS

This application is a national stage application (under 35 U.S.C. 371) of PCT/EP2003/010166 filed Sep. 12, 2003 which claims benefit to German application 102 42 636.8 filed Sep. 13, 2002.

The present invention relates to a process for preparing dialdehydes and/or ethylenically unsaturated monoaldehydes by hydroformylation of at least one compound having at least two ethylenically unsaturated double bonds in the presence of a catalyst comprising at least one complex of a metal of transition group VIII with at least one pnicogen ligand.

Ethylenically unsaturated monoaldehydes ("enals") and dialdehydes are industrially important intermediates. Thus, the aldehyde group can easily be converted into many other functional groups such as an amino group, a hydroxy group, a carboxy group, etc. Thus, many compounds which are difficult to obtain via other synthetic routes and are suitable as bifunctional synthetic building blocks for subsequent reactions can be obtained from enals. Dialdehydes and the diols, diamines and dicarboxylic acids obtained therefrom are suitable for many applications, e.g. for the preparation of polyesters and polyamides and also as crosslinkers for polymers.

The preparation of enals and dialdehydes by hydroformylation (oxo process) of compounds having at least two ethylenically unsaturated double bonds is known in principle. In this process, the ethylenically unsaturated compounds are reacted with carbon monoxide and hydrogen (synthesis gas) in the presence of a hydroformylation catalyst. The hydroformylation of multiply unsaturated compounds can result in the formation of mixtures of isomeric aldehydes depending on the position in which the CO molecules are added onto the double bonds. In addition, double bond isomerization can occur in the hydroformylation of diolefins having more than 4 carbon atoms or of triply and multiply unsaturated compounds. Owing to the great industrial importance of linear ethylenically unsaturated monoaldehydes, in particular those having a terminal double bond and aldehyde function ($\alpha,\omega$-enals), and of linear dialdehydes ($\alpha,\omega$-dialdehydes), there is a need for hydroformylation catalysts with give high yields of $\alpha,\omega$-enals and/or $\alpha,\omega$-dialdehydes starting from $\alpha,\omega$-ethylenically unsaturated compounds (e.g. $\alpha,\omega$-diolefins). For the purposes of the present invention, such catalysts will be referred to as catalysts having a high selectivity.

Hydroformylation catalysts are also required to have a good stability, both under the hydroformylation conditions and during the work-up, since catalyst losses have a highly adverse effect on the economics of the process. Furthermore, catalysts for the hydroformylation of multiply ethylenically unsaturated compounds should have a high activity at relatively low temperatures and relatively low reaction pressures in order to avoid undesirable secondary reactions such as the aldol reaction.

WO 95/30680 and van Leeuwen et al., organometallics 14, 3081 (1995) describe chelating phosphines having a xanthene backbone hose use in the rhodium-catalyzed hydroformylation of terminal olefins leads to high n-selectivities. Among the unsaturated compounds suitable for the hydroformylation, mention is made, inter alia, of diolefins.

Van der Slot et al., Organometallics 19, 2504 (2000), describe the synthesis of phosphoric diamide chelating ligands which have a bisphenol or xanthene backbone and whose diamide unit is formed by biuret groups, and also the catalytic properties of the rhodium complexes of these compounds in hydroformylation.

WO 00/56451 relates to cyclic oxaphosphorines which are substituted, inter alia, by pyrrole derivatives on the phosphorus atom and the use of these as ligands in hydroformylation catalysts.

WO 01/58589 describes compounds of phosphorus, arsenic and antimony based on diaryl-fused bicyclo[2.2.2] frameworks and catalysts in which these are present as ligands.

DE-A-100 23 471 describes a hydroformylation process which uses a hydroformylation catalyst comprising at least one phosphine ligand having two triarylphosphine groups, where one aryl radical of each of the two triarylphosphine groups is bound via a single bond to a nonaromatic 5- to 8-membered carbocyclic or heterocyclic bridging group. The phosphorus atoms can also bear, inter alia, hetaryl groups as further substituents.

DE-A-100 46 026 describes a hydroformylation process in which the catalyst used is a complex based on a phosphorus-, arsenic- or antimony-containing compound as ligand, where this compound has two groups which each contain a P, As or Sb atom and at least two further heteroatoms and are bound to a xanthene-like molecular framework.

U.S. Pat. No. 5,710,344 relates to the hydroformylation of olefins by means of rhodium catalysts which are modified with chelating phosphordiamidite ligands which have a bisphenol or bisnaphthol backbone and whose phosphorus atoms may bear unsubstituted pyrrolyl, imidazolyl or indolyl groups. As olefin, use is made of, inter alia, 1,3-butadiene.

In J. Organomet. Chem., 464 (1994), 107–111, A. M. Trzeciak and J. J. Ziolkowski describe the selective hydroformylation of 1,5-hexadiene and 1,7-octadiene in the presence of the catalyst systems $Rh(acac)(P(OC_6H_5)_3)_2/P(OC_6H_5)_3$ or $Rh(acac)(CO)(P(C_6H_5)_3)/P(C_6H_5)_3$. Here, the formation of many isomeric monoaldehydes and dialdehydes is observed. The n-selectivity of these catalyst systems is insufficient for the targeted preparation of $\alpha,\omega$-enals or -dialdehydes.

In J. Mol. Catal. A: Chem 2001, 175, 17–25, C. Botteghi et al. describe the preparation of long-chain linear dialdehydes by hydroformylation of $\alpha,\omega$-dienes or $\omega$-vinylaldehyde acetals. The selectivity with regard to linear $\alpha,\omega$-dialdehydes is low when standard catalyst systems such as $Rh(CO)_2(acac)$, $Rh(CO)_2(acac)P(C_6H_5)_3$ or $Rh(CO)_2(acac)P(OC_6H_5)_3$ are used. When a complex formed in situ from $RhH(CO)(P(C_6H_5)_3)_3$/xantphos is used as catalytic precursor, a high $\alpha,\omega$-diolefin conversion and a high proportion of linear dialdehyde are obtained. Disadvantages of this catalyst system are the very long reaction times and the large amounts of catalyst which have to be used.

WO 03/018192 describes a hydroformylation process using a catalyst complex which comprises as ligand at least one pyrrole-phosphorus compound in which a pyrrole groups which is substituted and/or integrated into a fused ring system is covalently bound via its pyrrole nitrogen atom to the phosphorus atom.

The international patent application PCT/EP03/01245, which is not a prior publication, describes chelating phosphorus compounds in which three nitrogen atoms which are themselves part of an aromatic ring system are covalently bound to each of the two phosphorus atoms, and their use as ligands for hydroformylation catalysts.

WO 02/083695 describes, inter alia, a process for the hydroformylation of olefins using a hydroformylation catalyst comprising a complex of a metal of transition group VIII with at least one chelating pnicogen compound as ligand.

These ligands have groups which contain two pnicogen atoms and are joined to one another via a xanthene-like or triptycene-like molecular framework, where at least one pyrrole group is covalently bound via its nitrogen atom to each pnicogen atom. As olefins suitable for the hydroformylation process, mention is made of many specific examples and also dienes or polyenes in general. Examples using these olefins are not described.

It is an object of the present invention to provide a process for the hydroformylation of compounds having at least two ethylenically unsaturated double bonds under relatively mild pressure and/or temperature conditions with short reaction times and/or catalyst loadings. In the hydroformylation of diolefins, a high proportion of α,ω-dialdehydes and/or α,ω-enals should preferably be obtained at a good conversion (high n-selectivity). The isomerization of ethylenically unsaturated double bonds in the molecule should be avoided if possible. In particular, the catalysts should also have long operating lives.

Surprisingly, we have found that this object is achieved by a hydroformylation process in which at least one complex of a metal of transition group VIII with at least one chelating pnicogen ligand, comprising two groups which contain pnicogen atoms and are joined to one another via a xanthene-like or triptycene-like molecular framework, is used as a hydroformylation catalyst, where at least one pyrrole group is covalently bound via its nitrogen atom to each pnicogen atom.

Figure 1:
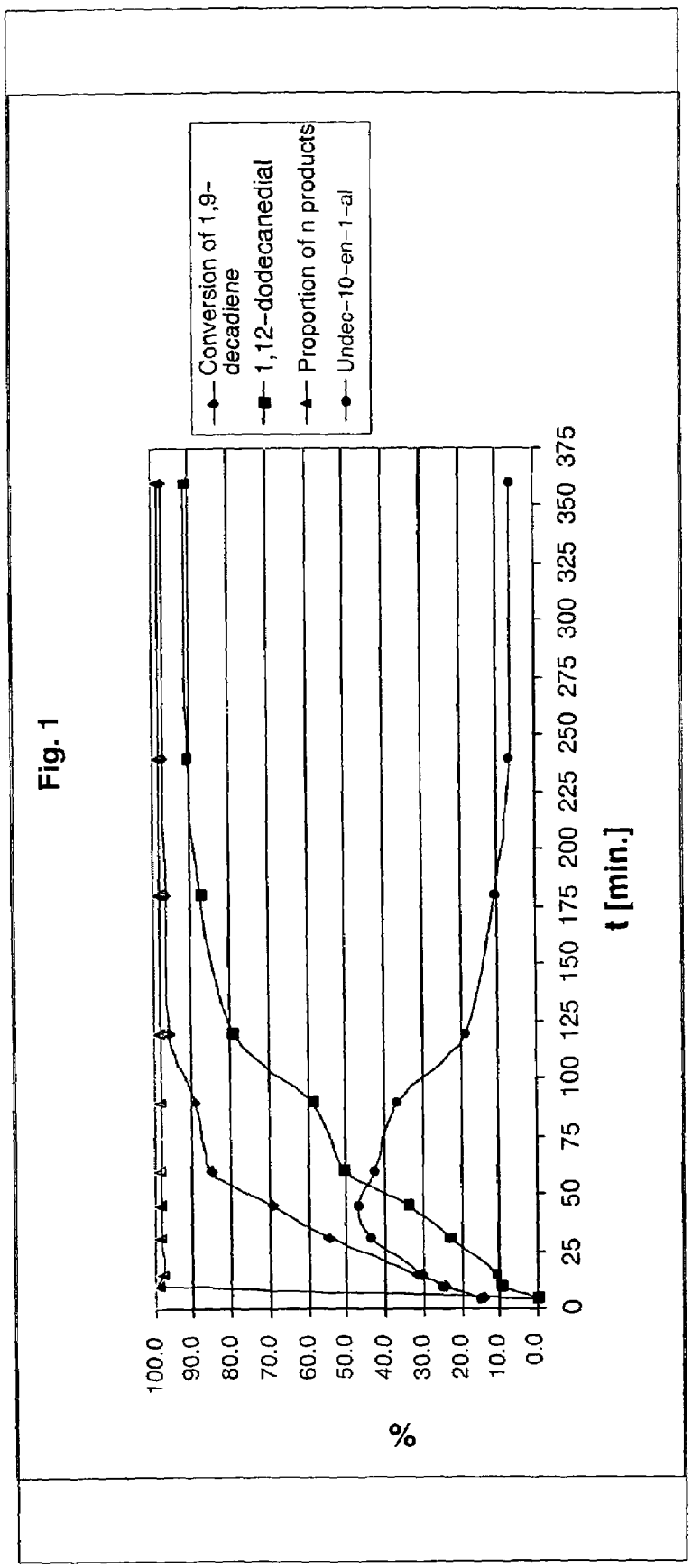
FIG. 1 shows a graphical presentation of example 5.

The present invention accordingly provides a process for preparing dialdehydes and/or ethylenically unsaturated monoaldehydes by reacting at least one compound having at least two ethylenically unsaturated double bonds with carbon monoxide and hydrogen in the presence of a hydroformylation catalyst comprising at least one complex of a metal of transition group VIII with at least one ligand selected from among chelating pnicogen compounds of the formula I,

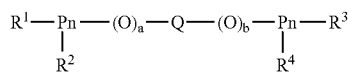

where
Q is a bridging group of the formula

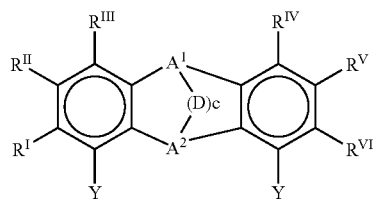

where
$A^1$ and $A^2$ are each, independently of one another, O, S, $SiR^aR^b$, $NR^c$ or $CR^dR^e$, where
$R^a$, $R^b$ and $R^c$ are each, independently of one another, hydrogen, alkyl, cycloalkyl, heterocycloalkyl, aryl or hetaryl, $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ form an intramolecular bridging group D, D is a divalent bridging group selected from among the groups

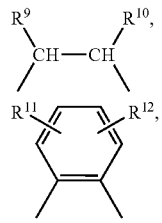 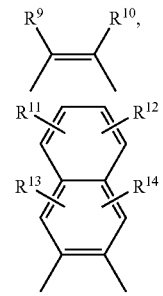

where
$R^9$ and $R^{10}$ are each, independently of one another, hydrogen, alkyl, cycloalkyl, aryl, halogen, trifluoromethyl, carboxyl, carboxylate or cyano or are joined to one another to form a $C_3$–$C_4$-alkylene bridge,
$R^{11}$, $R^{12}$, $R^{13}$ and $R^{14}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, acyl or nitro,
c is 0 or 1, (when c is 0, there is no direct bond between $A^1$ and $A^2$),
Y is a chemical bond,
$R^I$, $R^{II}$, $R^{III}$, $R^{IV}$, $R^V$ and $R^{VI}$ are each, independently of one another, hydrogen, alkyl, cycloalkyl, heterocycloalkyl, aryl, hetaryl, $COOR^f$, $COO$—$M^+$, $SO_3R^f$, $SO$—$_3M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano,
where
$R^f$, $E^1$, $E^2$ and $E^3$ are identical or different radicals selected from among hydrogen, alkyl, cycloalkyl and aryl,
$R^g$ is hydrogen, methyl or ethyl,
$M^+$ is a cation,
$X^-$ is an anion, and
x is an integer from 1 to 120,
or
two adjacent radicals selected from among $R^I$, $R^{II}$, $R^{III}$, $R^{IV}$, $R^V$ and $R^{VI}$ together with two adjacent carbon atoms of the benzene ring to which they are bound for a fused ring system having 1, 2 or 3 further rings,
a and b are each, independently of one another, 0 or 1,
Pn is a pnicogen atom selected from among the elements phosphorus, arsenic and antimony,
and
$R^1$, $R^2$, $R^3$, $R^4$ are each, independently of one another, hetaryl, hetaryloxy, alkyl, alkoxy, aryl, aryloxy, cycloalkyl, cycloalkoxy, heterocycloalkyl, heterocycloalkoxy or an $NE^1E^2$ group, with the proviso that $R^1$ and $R^3$ are pyrrole groups bound via the nitrogen atom to the pnicogen atom Pn
or $R^1$ together with $R^2$ and/or $R^3$ together with $R^4$ form a divalent group E of the formula Py—I—W where
Py is a pyrrole group which is bound via the pyrrole nitrogen atom to the pnicogen atom Pn,
I is a chemical bond or O, S, $SiR^aR^b$, $NR^c$, substituted or unsubstituted $C_1$–$C_{10}$-alkylene or $CR^hR^i$,
W is cycloalkyl, cycloalkoxy, aryl, aryloxy, hetaryl or hetaryloxy,
and
$R^h$ and $R^i$ are each, independently of one another, hydrogen, alkyl, cycloalkyl, heterocycloalkyl, aryl or hetaryl, or $R^1$ together with $R^2$ and/or $R^3$ together with $R^4$ form a bispyrrole group of the formula

bound via the nitrogen atoms to the pnicogen atom Pn.

In a specific embodiment, the present invention provides a process for the hydroformylation of compounds containing at least two ethylenically unsaturated double bonds, with isolation of the unsaturated monoaldehydes formed.

For the purpose of explaining the present invention, the expression "proportion of linear dialdehyde" (both double bonds are terminally hydroformylated) refers to the proportion of n,n-dialdehyde formed, based on the sum of the n,n-, n,iso- and iso,iso-dialdehydes formed. The proportion of n-products is thus given by the following equation:

$$\frac{\text{Proportion of}}{\text{n-products}} = \frac{\text{Proportion of n, n-dialdehyde formed}}{\text{Sum of all dialdehydes formed}}$$

Sum of all dialdehydes=Proportion of n,n-dialdehyde+Proportion of n,iso-dialdehyde+Proportion of iso,iso-dialdehyde For the purpose of explaining the present invention, the expression 'alkyl' encompasses straight-chain and branched alkyl groups. These are preferably straight-chain or branched $C_1$–$C_{20}$-alkyl groups, more preferably $C_1$–$C_{12}$-alkyl groups, particularly preferably $C_1$–$C_8$-alkyl groups and very particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The expression "alkyl" also encompasses substituted alkyl groups which can generally bear 1, 2, 3, 4, or 5 substituents, preferably 1, 2 or 3 and particularly preferably 1 substituent, selected from among cycloalkyl, aryl, hetaryl, halogen, $NE^1E^2$, $NE^1E^2E^{3+}$, carboxyl, carboxylate, —$SO_3H$ and sulfonate.

For the purposes of the present invention, the expression "alkylene" refers to straight-chain or branched alkanediyl groups having from 1 to 4 carbon atoms.

For the purposes of the present invention, the expression "cycloalkyl" refers to both unsubstituted and substituted cycloalkyl groups, preferably $C_5$–$C_7$-cycloalkyl groups such as cyclopentyl, cyclohexyl or cycloheptyl, which if substituted can generally bear 1, 2, 3, 4 or 5 substituents, preferably 1, 2 or 3 substituents and particularly preferably 1 substituent, selected from among alkyl, alkoxy and halogen.

For the purposes of the present invention, the expression "heterocycloalkyl" encompasses saturated, cycloaliphatic groups which generally have from 4 to 7, preferably 5 or 6, ring atoms and in which 1 or 2 of the ring carbons are replaced by heteroatoms selected from among the elements oxygen, nitrogen and sulfur and which may, if desired, be substituted, where substituted heterocycloaliphatic groups can bear 1, 2 or 3 substituents, preferably 1 or 2 substituents, particularly preferably 1 substituent, selected from among alkyl, aryl, $COOR^f$, $COO—M^+$ and $NE^1E^2$, preferably alkyl. Examples of such heterocycloaliphatic groups are pyrrolidinyl, piperidinyl, 2,2,6,6-tetramethylpiperidinyl, imidazolidinyl, pyrazolidinyl, oxazolidinyl, morpholidinyl, thiazolidinyl, isothiazolidinyl, isoxazolidinyl, piperazinyl, tetrahydrothiophenyl, tetrahydrofuranyl, tetrahydropyranyl, dioxanyl.

For the purposes of the present invention, the expression "aryl" encompasses both unsubstituted and substituted aryl groups and preferably refers to phenyl, tolyl, xylyl, mesityl, naphthyl, fluorenyl, anthracenyl, phenanthrenyl or naphthacenyl, particularly preferably phenyl or naphthyl, where substituted aryl groups can generally bear 1, 2, 3, 4 or 5 substituents, preferably 1, 2 or 3 substituents and particularly preferably 1 substituent, selected from among alkyl, alkoxy, carboxyl, carboxylate, trifluoromethyl, —$SO_3H$, sulfonate, $NE^1E^2$, alkylene-$NE^1E^2$, nitro, cyano and halogen.

For the purposes of the present invention, the expression "hetaryl" encompasses unsubstituted or substituted heterocycloaromatic groups, preferably the groups pyridyl, quinolinyl, acridinyl, pyridazinyl, pyrimidinyl, pyrazinyl and also the subgroups of "pyrrole groups", where substituted heterocycloaromatic groups can generally bear 1, 2 or 3 substituents selected from among alkyl, alkoxy, carboxyl, carboxylate, —$SO_3H$, sulfonate, $NE^1E^2$, alkylene-$NE^1E^2$, trifluoromethyl and halogen.

For the purposes of the present invention, the expression "pyrrole group" refers to a series of unsubstituted or substituted, heterocycloaromatic groups which are derived structurally from the basic pyrrole skeleton and which contain, in the heterocycle, a pyrrole nitrogen atom which can be covalently bound to other atoms, for example a pnicogen atom. The expression "pyrrole group" thus encompasses the unsubstituted or substituted groups pyrrolyl, imidazolyl, pyrazolyl, indolyl, purinyl, indazolyl, benzotriazolyl, 1,2,3-triazolyl, 1,3,4-triazolyl and carbazolyl which if substituted can generally bear 1, 2 or 3 substituents, preferably 1 or 2 substituents, particularly preferably 1 substituent, selected from among alkyl, alkoxy, acyl, carboxyl, carboxylate, —$SO_3H$, sulfonate, $NE^1E^2$, alkylene-$NE^1E^2$, trifluoromethyl and halogen.

Accordingly, the expression "bispyrrole group" as used for the purposes of the present invention encompasses divalent groups of the formula

which comprise two pyrrole groups linked via a direct chemical bond or via alkylene, oxa, thia, imino, silyl or alkylimino groups, for example the bisindolediyl group of the formula

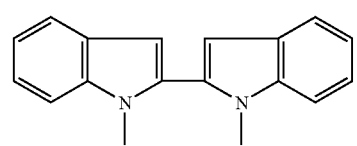

as an example of a bispyrrole group which comprises two directly linked pyrrole groups, in this case indolyl, or the bispyrrolediylmethane group of the formula

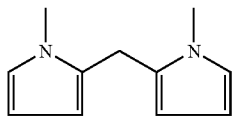

as an example of a bispyrrole group comprising two pyrrole groups, in this case pyrrolyl, linked via a methylene group. Like the pyrrole groups, the bispyrrole groups can also be unsubstituted or substituted and if substituted generally bear 1, 2 or 3 substituents, preferably 1 or 2 substituents, in particular 1 substituent, selected from-among alkyl, alkoxy, carboxyl, carboxylate, —$SO_3H$, sulfonate, $NE^1E^2$, alkylene-$NE^1E^2$, trifluoromethyl and halogen, per pyrrole group unit. In these indications of the number of possible substituents, the link between the pyrrole group units via a direct chemical bond or via the groups mentioned above is not regarded as substitution.

Carboxylate and sulfonate are, for the purposes of the present invention, preferably a derivative of a carboxylic acid function or a sulfonic acid function, in particular a metal carboxylate or sulfonate, a carboxylic or sulfonic ester function or a carboxamide or sulfonamide function. They include, for example, the esters with $C_1$–$C_4$-alkanols such as methanol, ethanol, n-propanol, isopropanol, n-butanol, sec-butanol and tert-butanol.

What has been said above regarding the expressions "alkyl", "cycloalkyl", "aryl", "heterocycloalkyl" and "hetaryl" applies analogously to the expressions "alkoxy", "cycloalkoxy", "aryloxy", "heterocycloalkoxy" and "hetaryloxy".

For the purposes of the present invention, the expression "acyl" refers to alkanoyl or aroyl groups generally having from 2 to 11, preferably from 2 to 8, carbon atoms, for example the acetyl, propionyl, butyryl, pentanoyl, hexanoyl, heptanoyl, 2-ethylhexanoyl, 2-propylheptanoyl, benzoyl or naphthoyl groups.

The groups $NE^1E^2$ and $NE^4E^5$ are preferably N,N-dimethylamino, N,N-diethylamino, N,N-dipropylamino, N,N-diisopropylamino, N,N-di-n-butylamino, N,N-di-t-butylamino, N,N-dicyclohexylamino or N,N-diphenylamino.

Halogen is fluorine, chlorine, bromine or iodine, preferably fluorine, chlorine or bromine.

$M^+$ is a cation equivalent, i.e. a monovalent cation or the part of a polyvalent cation corresponding to a single positive charge. The cation $M^+$ serves merely as counterion to neutralize negatively charged substituent groups such as the COO— or sulfonate group and can in principle be selected freely. Preference is therefore given to using alkali metal ions, in particular $Na^+$, $K^+$—, $Li^+$ ions, or onium ions such as ammonium, monoalkylammonium, dialkylammonium, trialkylammonium, tetraalkylammonium, phosphonium, tetraalkylphosphonium or tetraarylphosphonium ions.

An analogous situation applies to the anion equivalent X— which merely serves as counterion to positively charged substituent groups such as ammonium groups and can be selected freely from among monovalent anions and the part of a polyvalent anion corresponding to a single negative charge, with preference generally being given to halide ions X—, in particular chloride and bromide.

x is an integer from 1 to 240, preferably an-integer from 3 to 120.

Fused ring systems can be aromatic, hydroaromatic and cyclic compounds joined by fusion. Fused ring systems comprise two, three or more rings. Depending on the way in which the rings of fused ring systems are linked, a distinction is made between ortho-fusion, i.e. each ring shares an edge or two atoms with each adjacent ring, and peri-fusion, in which a carbon atom belongs to more than two rings. Among the fused ring systems, preference is given to ortho-fused ring systems.

Y is a chemical bond, i.e. the linkage point of the bridging group Q to the groups —O—, or in the case of a and/or b being 0, to the groups $PnR^1R^2$ or $PnR^3R^4$.

In the bridging group Q, the groups $A^1$ and $A^2$ can generally each be, independently of one another, O, S, $SiR^aR^b$, $NR^c$ or $CR^dR^e$, where the substituents $R^a$, $R^b$ and $R^c$ are generally each, independently of one another, hydrogen, alkyl, cycloalkyl, heterocycloalkyl, aryl or hetaryl, while the groups $R^d$ and $R^e$ are each, independently of one another, hydrogen, alkyl, cycloalkyl, heterocycloalkyl, aryl or hetaryl or the group $R^d$ together with a further group $R^d$ or the group $R^e$ together with a further group $R^e$ may form an intramolecular bridging group D.

D is a divalent bridging group which is generally selected from among the groups

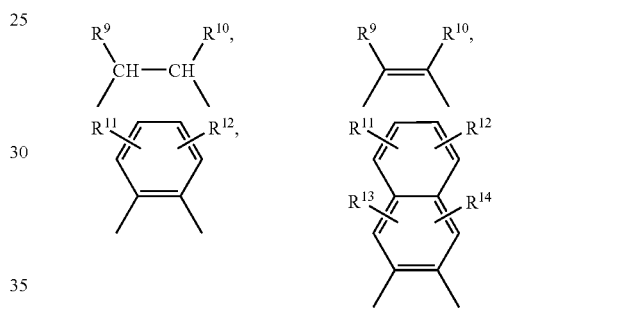

where $R^9$ and $R^{10}$ are each, independently of one another, hydrogen, alkyl, cycloalkyl, aryl, halogen, trifluoromethyl, carboxyl, carboxylate or cyano or are joined to one another to form a $C_3$–$C_4$-alkylene group and $R^{11}$, $R^{12}$, $R^{13}$ and $R^{14}$ are each, independently of one another, hydrogen, alkyl, cycloalkyl, aryl, halogen, trifluoromethyl, COOH, carboxylate, cyano, alkoxy, $SO_3H$, sulfonate, $NE^1E^2$, alkylene-$NE^1E^2E^{3+}X^-$, aryl or nitro. Preference is given to the groups $R^9$ and $R^{10}$ each being hydrogen, $C_1$–$C_{10}$-alkyl or carboxylate and the groups $R^{11}$, $R^{12}$, $R^{13}$ and $R^{14}$ each being hydrogen, $C_1$–$C_{10}$-alkyl, halogen, in particular fluorine, chlorine or bromine, trifluoromethyl, $C_1$–$C_4$-alkoxy, carboxylate, sulfonate or $C_6$–$C_{14}$-aryl. $R^9$, $R^{10}$, $R^{11}$, $R^{12}$, $R^{13}$ and $R^{14}$ are particularly preferably each hydrogen. For use in an aqueous reaction medium, preference is given to chelating pnicogen compounds in which 1, 2 or 3, preferably 1 or 2, in particular 1, of the groups $R^{11}$, $R^{12}$, $R^{13}$ and/or $R^{14}$ are/is a COO—$Me^+$, $SO_{3-M}^+$ or $NE^1E^2E^{3+}X^-$ group, where $M^+$ and $X^-$ are as defined above.

Particularly preferred bridging groups D are the ethylene group

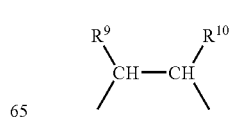

and the 1,2-phenylene group

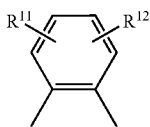

When $R^d$ together with a further group $R^d$ or $R^e$ together with a further group $R^e$ forms an intramolecular bridging group D, the index c is in this case equal to 1.

Preferred bridging groups Q include, in addition to those having a triptycene-like carbon skeleton, ones in which the index c is 0 and the groups $A^1$ and $A^2$ are selected from among the groups O, S and $CR^dR^e$, in particular from among O, S, the methylene group ($R^d=R^e=H$), the dimethylmethylene group ($R^d=R^e=CH_3$), the diethylmethylene group ($R^d=R^e=C_2H_5$), the di-n-propylmethylene group ($R^d=R^e=$n-propyl) or the di-n-butylmethylene group ($R^d=R^e=$n-butyl). Particular preference is given to those bridging groups Q in which $A^1$ is different from $A^2$, with $A^1$ preferably being a $CR^dR^e$ group and $A^2$ preferably being an O or S group, particularly preferably an oxa group O.

Particularly preferred bridging groups Q are thus those which are built up of a triptycene-like or xanthene-like ($A^1:CR^dR^e, A^2:O$) framework.

The substituents $R^I$, $R^{II}$, $R^{III}$, $R^{IV}$, $R^V$ and $R^{VI}$ are preferably selected from among hydrogen, alkyl, alkoxy, cycloalkyl, heterocycloalkyl, aryl and hetaryl. In a first preferred embodiment, $R^I$, $R^{II}$, $R^{III}$, $R^{IV}$, $R^V$ and $R^{VI}$ are each hydrogen. In a further preferred embodiment, $R^I$ and $R^{VI}$ are each, independently of one another, $C_1$–$C_4$-alkyl or $C_1$–$C_4$-alkoxy. $R^I$ and $R^{VI}$ are preferably selected from among methyl, ethyl, isopropyl, tert-butyl and methoxy. In these compounds, $R^{II}$, $R^{III}$, $R^{IV}$ and $R^V$ are preferably each hydrogen. In a further preferred embodiment, $R^{II}$ and $R^V$ are each, independently of one another, $C_1$–$C_4$-alkyl or $C_1$–$C_4$-alkoxy. $R^{II}$ and $R^V$ are preferably selected from among methyl, ethyl, isopropyl, tert-butyl and methoxy. In these compounds, $R^I$, $R^{III}$, $R^{IV}$ and $R^{VI}$ are preferably each hydrogen.

When two adjacent radicals selected from among $R^I$, $R^{II}$, $R^{III}$, $R^{IV}$, $R^V$ and $R^{VI}$ form a fused-on ring system, they preferably form a benzene or naphthalene group. Fused-on benzene rings are preferably unsubstituted or have 1, 2 or 3, in particular 1 or 2, substituents selected from among alkyl, alkoxy, halogen, $SO_3H$, sulfonate, $NE^1E^2$, alkylene-$NE^1E^2$, trifluoromethyl, nitro, $COOR^f$, alkoxycarbonyl, acyl and cyano. Fused-on naphthalene units are preferably unsubstituted or bear a total of 1, 2 or 3, in particular 1 or 2, of the substituents mentioned above in the case of the fused-on benzene rings in the ring which is not fused on and/or in the fused-on ring.

If the use of the chelating pnicogen compounds used according to the present invention in a hydroformylation medium is envisaged, at least one of the radicals $R^I$, $R^{II}$, $R^{III}$, $R^{IV}$, $R^V$ and/or $R^{VI}$ is a polar (hydrophilic) group, which generally results in water-soluble pnicogen chelate complexes being formed with a group VIII metal. The polar groups are preferably selected from among $COOR^f$, COO⁻M⁺, $SO_3R^f$, $SO_3^-{}_M^+$, $NE^1E^2$, alkylene-$NE^1E^2$, $NE^1E^2E^{3+}$X⁻, alkylene-$NE^1E^2E^{3+}$X⁻, $OR^f$, $SR^f$, $(CHR^gCH_2O)_xR^f$ or $(CH_2CH_2N(E^1))_xR^f$, where $R^f$, $E^1$, $E^2$, $E^3$, $R^g$, $M^+$, $X^-$ and x are as defined above.

The bridging group Q is either bound directly via the chemical bond Y or via an oxa group O to the groups $PnR^1R^2$ and $PnR^3R^4$.

Pn is an atom of the pnicogen group, selected from among phosphorus, arsenic and antimony. Pn is particularly preferably phosphorus.

The individual pnicogen atom Pn of the chelating pnicogen compounds used according to the present invention are each bound via two covalent bonds to two substituents $R^1$ and $R^2$ or $R^3$ and $R^4$, with the substituents $R^1$, $R^2$, $R^3$ and $R^4$ each being able to be, independently of one another, hetaryl, hetaryloxy, alkyl, alkoxy, aryl, aryloxy, cycloalkyl, cycloalkoxy, heterocycloalkyl, heterocycloalkoxy or an $NE^1E^2$ group, with the proviso that $R^1$ and $R^3$ are pyrrole groups bound via the pyrrole nitrogen atom to the pnicogen atom Pn. The substituents $R^2$ and/or $R^4$ are advantageously also pyrrole groups bound via the pyrrole nitrogen atom to the pnicogen atom Pn. It can also be advantageous for the substituent $R^1$ together with the substituent $R^2$ and/or the substituent $R^3$ together with the substituent $R^4$ to form a bispyrrole group bound via the pyrrole nitrogen atoms to the pnicogen atom Pn.

The meaning of the individual expressions used in the preceding paragraph corresponds to the definition given above.

In a preferred embodiment, the process of the present invention is carried using out a hydroformylation catalyst in which the radicals $R^1$, $R^2$, $R^3$ and $R^4$ are selected independently from among groups of the formulae I.a to I.k:

(I.a)

(I.b)

(I.c)

(I.d)

(I.e)

(I.f)

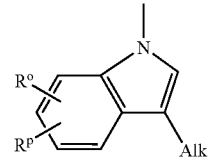

-continued
(I.g) 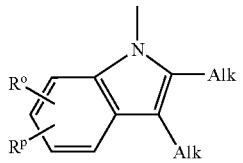
(I.h) 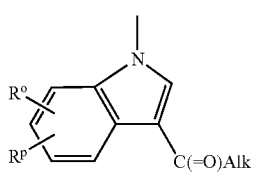
(I.i) 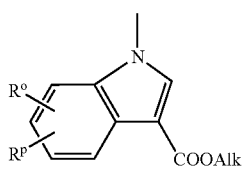
(I.k) 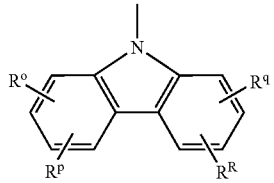
where
Alk is a $C_1$–$C_4$-alkyl group and
$R^o$, $R^p$, $R^q$ and $R^r$ are each, independently of one another, hydrogen, $C_1$–$C_4$-alkyl, $C_1$–$C_4$-alkoxy, acyl, halogen, trifluoromethyl, $C_1$–$C_4$-alkoxycarbonyl or carboxyl.
For the purposes of illustration, a few advantageous pyrrole groups are listed below:
(I.a1) 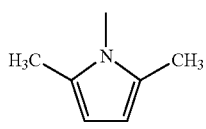
(I.a2) 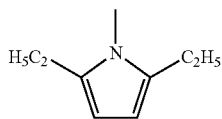
(I.b1) 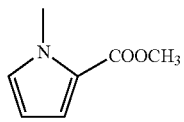
(I.b2) 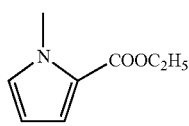
(I.c1) 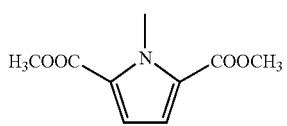
(I.c2) 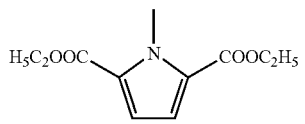
(I.d1) 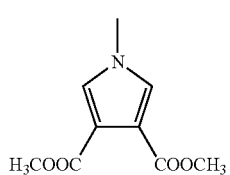
(I.d2) 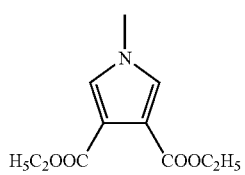
(I.e1) 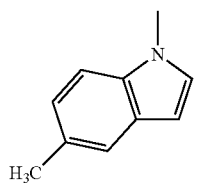
(I.e2) 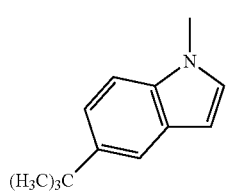
(I.e3) 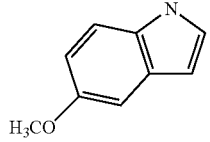
(I.f1) 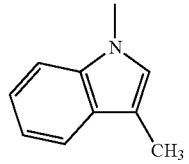
(I.f2) 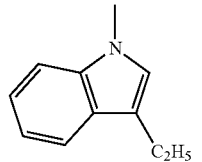
(I.f3) 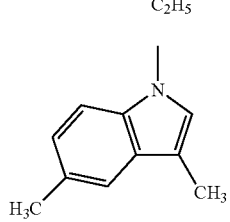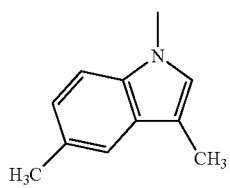

-continued

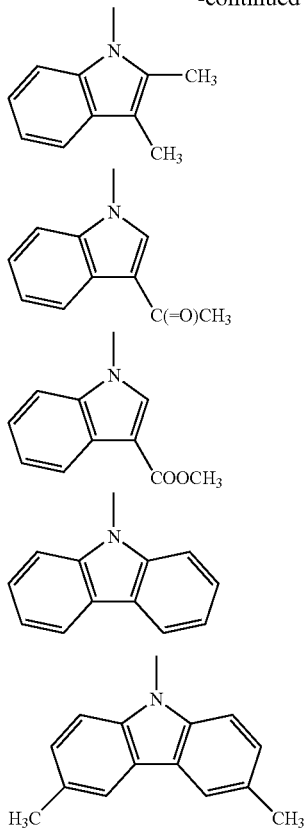

(I.g1)
(I.h1)
(I.i1)
(I.k1)
(I.k2)

The 3-methylindolyl group (skatolyl group) of the formula I.f1 is particularly advantageous. Hydroformylation catalysts based on ligands having one or more 3-methylindolyl group(s) bound to the phosphorus atom have a particularly high stability and thus display particularly long catalyst operating lives.

In a further advantageous embodiment of the present invention, the substituent $R^1$ together with the substituent $R^2$ or the substituent $R^3$ together with the substituent $R^4$ can form a divalent group of the formula Py—I—W containing a pyrrole group bound via the pyrrole nitrogen atom to the pnicogen atom Pn, where Py is a pyrrole group, I is a chemical bond or O, S, $SiR^aR^b$, $NR^c$ or $CR^hR^i$, W is cycloalkyl, cycloalkoxy, aryl, aryloxy, hetaryl or hetaryloxy and $R^h$ and $R^i$ are each, independently of one another, hydrogen, alkyl, cycloalkyl, heterocycloalkyl, aryl or hetaryl, where the expressions used have the meanings given above.

Preferred divalent groups of the formula

Py—I—W are, for example,

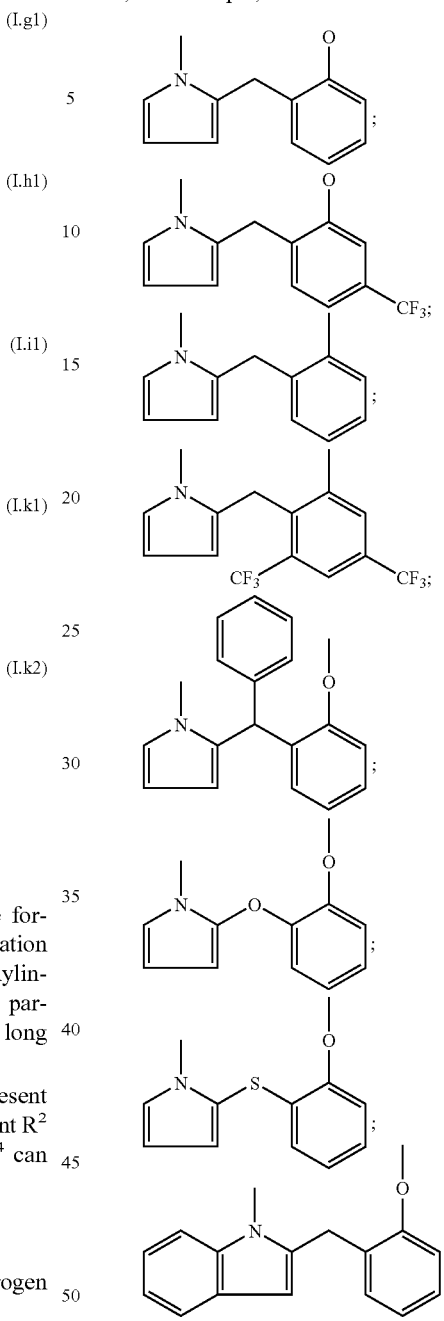

In the process of the present invention, preference is given to using hydroformylation catalysts comprising at least one ligand of the formula I in which the substituent $R^1$ together with the substituent $R^2$ or the substituent $R^3$ together with the substituent $R^4$ forms a bispyrrole group of the formula or -continued

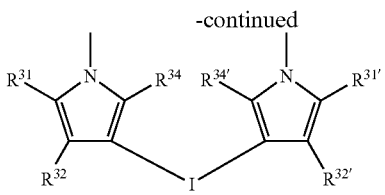

where

I is a chemical bond or O, S, $SiR^aR^b$, $NR^c$ or substituted or unsubstituted $C_1$–$C_{10}$-alkylene, preferably $CR^hR^i$, where $R^a$, $R^b$, $R^c$, $R^h$ and $R^i$ are each, independently of one another, hydrogen, alkyl, cycloalkyl, heterocycloalkyl, aryl or hetaryl, $R^{31}$, $R^{31'}$, $R^{32}$, $R^{32'}$, $R^{33}$, $R^{33'}$, $R^{34}$ and $R^{34'}$ are each, independently of one another, hydrogen, alkyl, cycloalkyl, heterocycloalkyl, aryl, hetaryl, W'COOR$^a$, W'COO—M$^+$, W'($SO_3$)R$^f$, W'($SO_3$)—M$^+$, W'PO$_3$(R$^f$)(R$^g$), W'(PO$_3$)$^{2-}$(M$^+$)$_2$, W'NE$^1$E$^2$, W'(NE$^1$E$^2$E$^3$)$^+$X$^-$, W'OR$^f$, W'SR$^f$, (CHR$^g$CH$_2$O)$_x$R$^f$, (CH$_2$NE$^1$)$_x$R$^f$, (CH$_2$CH$_2$NE$^1$)$_x$R$^f$, halogen, trifluoromethyl, nitro, acyl or cyano, where W' is a single bond, a heteroatom or a divalent bridging group having from 1 to 20 bridge atoms, R$^f$, E$^1$, E$^2$, E$^3$ are identical or different radicals selected from among hydrogen, alkyl, cycloalkyl and aryl, R$^g$ is hydrogen, methyl or ethyl, M$^+$ is a cation equivalent, X$^-$ is an anion equivalent and x is an integer from 1 to 240, where two adjacent radicals $R^{31}$ and $R^{32}$ and/or $R^{31'}$ and $R^{32'}$ together with the carbon atoms of the pyrrole ring to which they are bound may also form a fused ring system having 1, 2 or 3 further rings.

I is preferably a chemical bond or a $C_1$–$C_4$-alkylene group, particularly preferably a methylene group.

For the purposes of illustration, a few advantageous "bispyrrolyl groups" are listed below:

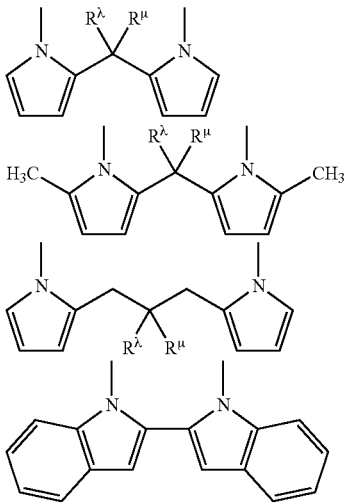

a: $R^λ$, $R^μ$ = H
b: $R^λ$ = H
   $R^μ$ = $C_6H_5$
c: ($R^λ$ + $R^μ$) = $C_4H_8$

In a preferred embodiment, the chelating pnicogen compounds used according to the present invention are selected from among compounds of the formula II

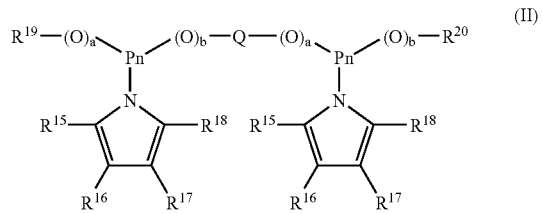

where $R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO—M$^+$, W'($SO_3$)R$^k$, W'($SO_3$)—M$^+$, W'PO$_3$(R$^k$) (R$^1$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, where W' is a single bond, a heteroatom or a divalent bridging group having from 1 to 20 bridge atoms, R$^k$, E$^4$, E$^5$, E$^6$ are identical or different radicals selected from among hydrogen, alkyl, cycloalkyl and aryl, $R^1$ is hydrogen, methyl or ethyl, M$^+$ is a cation equivalent, X$^-$ is an anion equivalent and y is an integer from 1 to 240, where two adjacent radicals $R^{15}$, $R^{16}$, $R^{17}$ and $R^{18}$ together with the carbon atoms of the pyrrole ring to which they are bound may also form a fused ring system having 1, 2 or 3 further rings, with the proviso that at least one of the radicals $R^{15}$, $R^{16}$, $R^{17}$ and $R^{18}$ is not hydrogen and $R^{19}$ and $R^{20}$ are not joined to one another, $R^{19}$ and $R^{20}$ are each, independently of one another, cycloalkyl, heterocycloalkyl, aryl or hetaryl, a and b are each, independently of one another, 0 or 1, Pn is a pnicogen atom selected from among the elements phosphorus, arsenic and antimony, preferably phosphorus, Q is a bridging group as defined above.

In the compounds of the formula II, the pnicogen atoms Pn are preferably both phosphorus.

As regards useful and preferred embodiments of the bridging group Q, what has been said above is fully incorporated by reference at this point.

The radicals $R^{15}$ to $R^{18}$ can, independently of one another, each have identical or different meanings.

Preference is given to compounds of the formula II in which one or two of the radicals $R^{15}$, $R^{16}$, $R^{17}$ and $R^{18}$ in the pyrrole groups is/are each one of the abovementioned substituents which are different from hydrogen and the remainder are hydrogen.

Preference is also given to compounds of the formula II in which the pyrrole groups bear a substituent different from hydrogen in the 2 position, the 2,5 positions or the 3,4 positions.

The substituents $R^{15}$ to $R^{18}$ which are different from hydrogen are preferably selected independently from among $C_1$–$C_8$-alkyl, preferably $C_1$–$C_4$-alkyl, especially methyl, ethyl, isopropyl and tert-butyl, alkoxycarbonyl such as methoxycarbonyl, ethoxycarbonyl, isopropyloxycarbonyl and tert-butyloxycarbonyl and trifluoromethyl.

Preference is given to compounds of the formula II in which the radicals $R^{15}$ and $R^{16}$ and/or $R^{17}$ and $R^{18}$ together with the carbon atoms of the pyrrole ring to which they are bound form a fused ring system having 1, 2 or 3 further rings. When $R^{15}$ and $R^{16}$ and/or $R^{17}$ and $R^{18}$ form a fused-on ring system, they preferably form benzene or naphthalene groups. Fused-on benzene rings are preferably unsubstituted or have 1, 2 or 3, in particular 1 or 2, substituents selected from among alkyl, alkoxy, halogen, $SO_3H$, sulfonate, $NE^4E^5$, alkylene-$NE^4E^5$, trifluoromethyl, nitro, $COOR^k$, alkoxycarbonyl, acyl and cyano. Fused-on naphthalene units are preferably unsubstituted or bear 1, 2 or 3, in particular 1 or 2, of the substituents mentioned above in the case of the fused-on benzene rings in the ring which is not fused on and/or in the fused-on ring. When $R^{15}$ and $R^{16}$ form a fused-on ring system, then $R^{17}$ and $R^{18}$ are preferably each hydrogen or $R^{18}$ is hydrogen and $R^{17}$ is a substituent selected from among $C_1$–$C_8$-alkyl, preferably $C_1$–$C_4$-alkyl, especially methyl, ethyl, isopropyl or tert-butyl.

If use of the compounds of the formula II in an aqueous hydroformylation medium is envisaged, at least one of the radicals $R^{15}$, $R^{16}$, $R^{17}$ and/or $R^{18}$ is/are each a polar (hydrophilic) group, which generally results in water-soluble complexes with a group VIII metal. The polar groups are preferably selected from among $COOR^k$, COO—$M^+$, $SO_3R^k$, $SO_3$—$M^+$, $NE^4E^5$, alkylene-$NE^4E^5$, $NE^4E^5E^{6+}X^-$, alkylene-$NE^4E^5E^{6+}X^-$, $OR^k$, $SR^k$, $(CHR^1CH_2O)_yR^k$ or $(CH_2CH_2N(E^4))_yR^k$, where $R^k$, $E^4$, $E^5$, $E^6$, $R^l$, $M^+$, $X^-$ and y are as defined above.

The compounds of the formula II are preferably selected from among compounds of the formulae II.1 to II.3

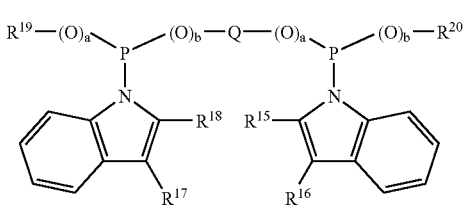
(II.1)

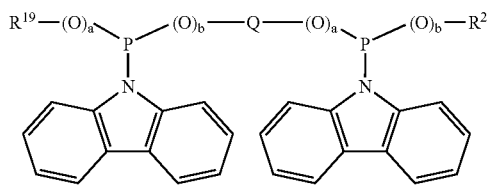
(II.2)

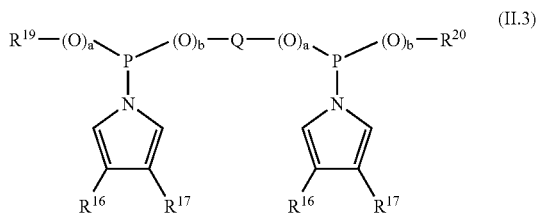
(II.3)

where $R^{15}$, $R^{16}$, $R^{17}$, $R^{18}$, Q, a and b are as defined above, where at least one of the radicals $R^{16}$ and $R^{17}$ in the formula II.3 is not hydrogen, $R^{19}$ and $R^{20}$ are each, independently of one another, cycloalkyl, heterocycloalkyl, aryl or hetaryl.

In the compounds of the formula II.1, the radicals $R^{15}$ to $R^{18}$ are preferably all hydrogen. Preference is also given to $R^{15}$ and $R^{18}$ each being hydrogen and $R^{16}$ and $R^{17}$ being selected from among $C_1$–$C_8$-alkyl, preferably $C_1$–$C_4$-alkyl, for example methyl, ethyl, isopropyl and tert-butyl.

In the compounds of the formula II.3, the radicals $R^{16}$ and $R^{17}$ are preferably selected from among $C_1$–$C_8$-alkyl, particularly preferably $C_1$–$C_4$-alkyl such as methyl, ethyl, isopropyl and tert-butyl, and $COOR^k$, where $R^k$ is $C_1$–$C_4$-alkyl such as methyl, ethyl, isopropyl or tert-butyl.

Purely for the purposes of illustration, a few advantageous examples of advantageous chelating pnicogen compounds to be used according to the present invention are listed below:

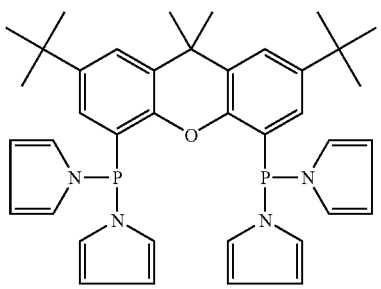
1

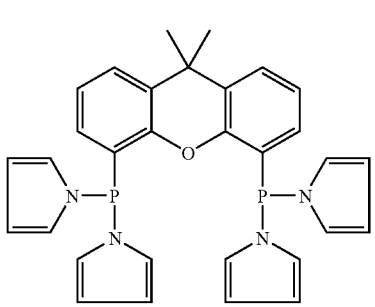
2

-continued
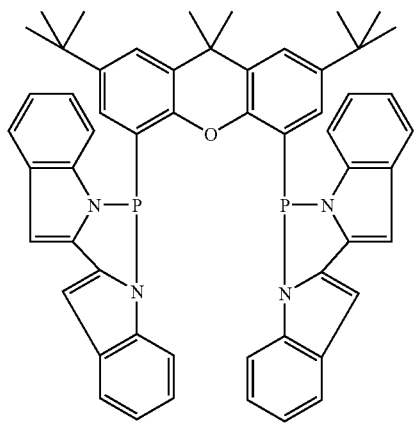
3
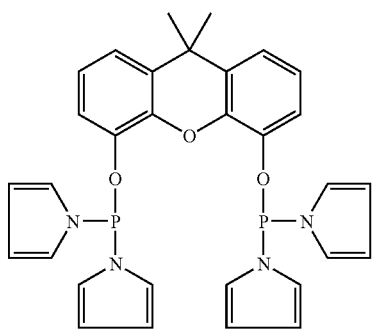
4
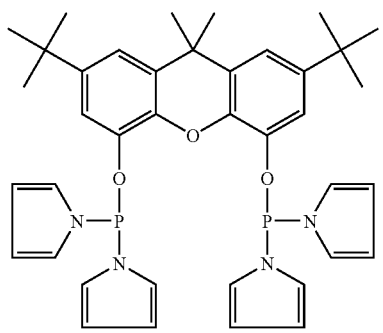
5
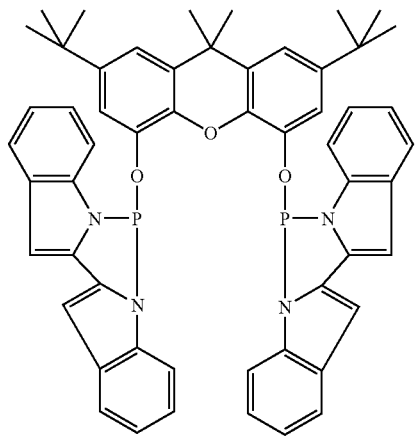
6
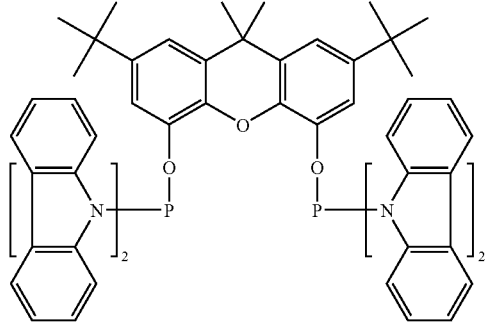
7
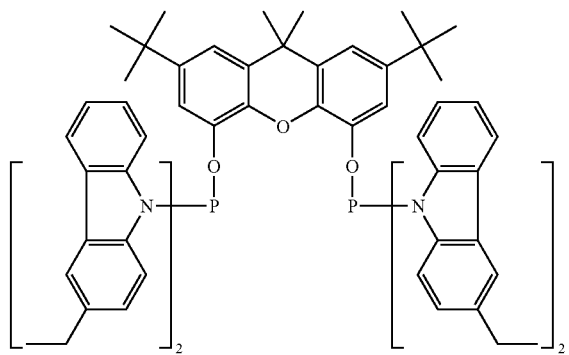
8
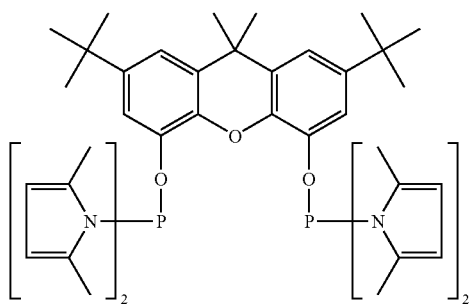
9

-continued
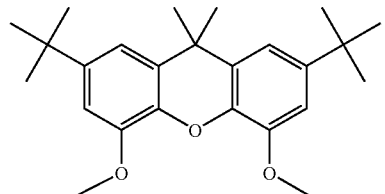
10
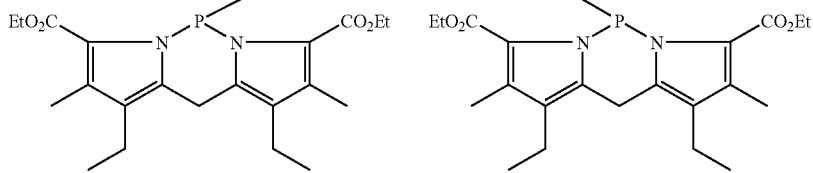
11
12
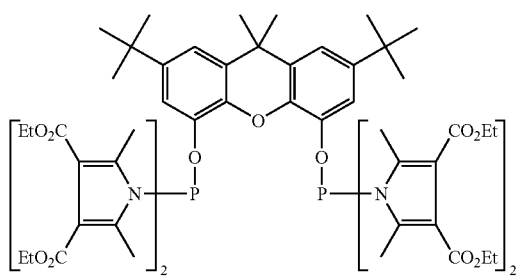
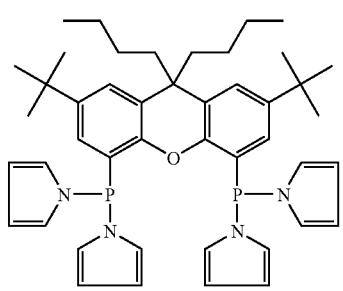
13
14
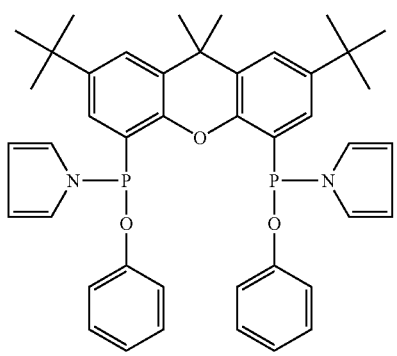
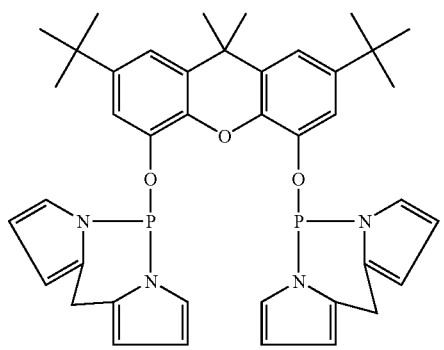
15
16
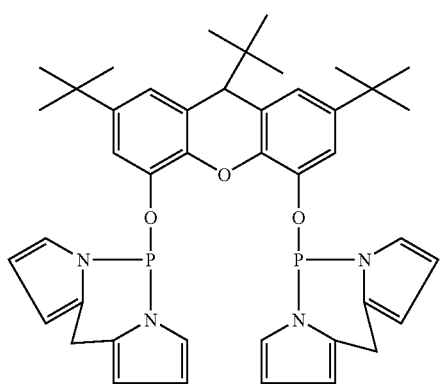
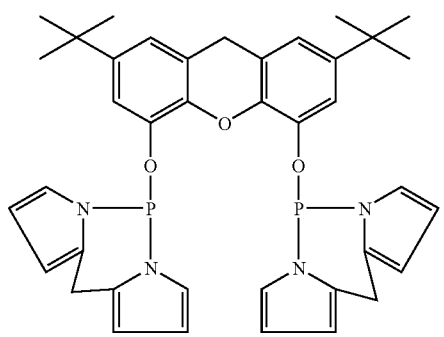

-continued
17
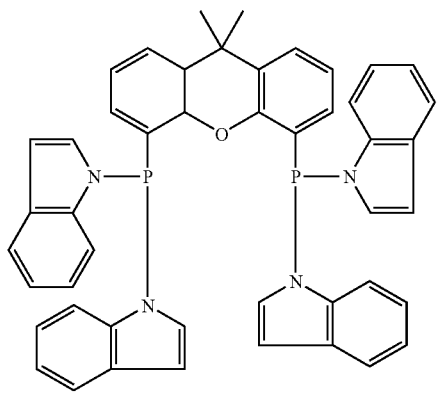
18
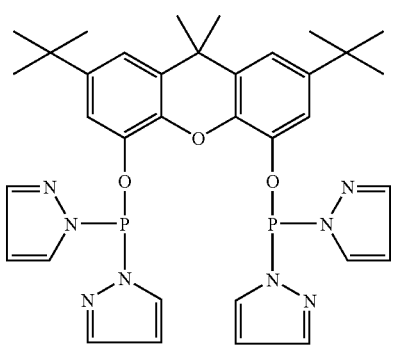
19
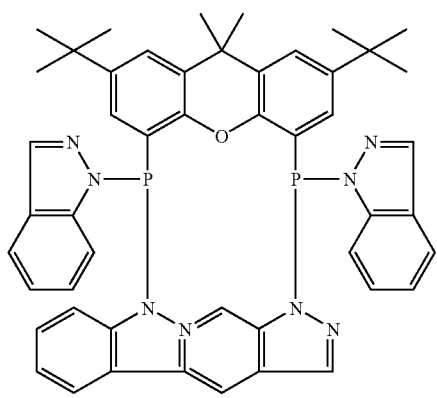
20
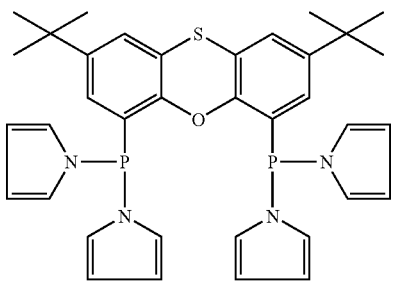
21
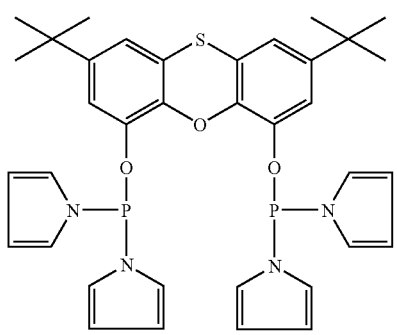
22
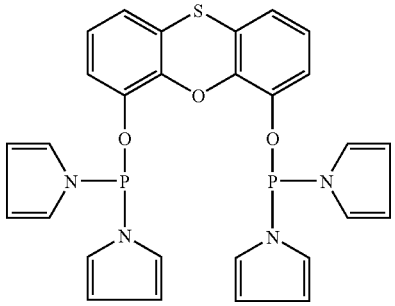
23
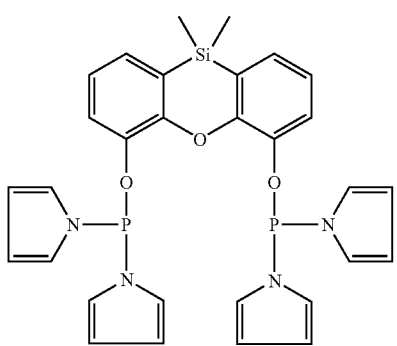
24
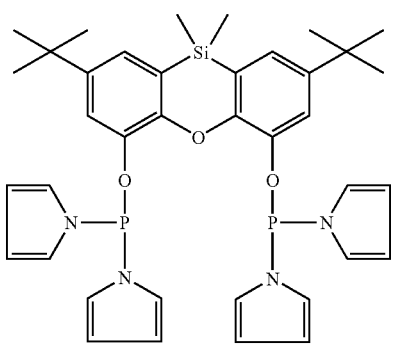

-continued
25
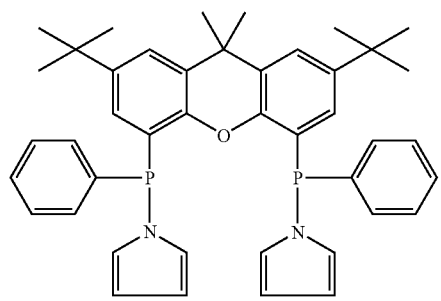
26
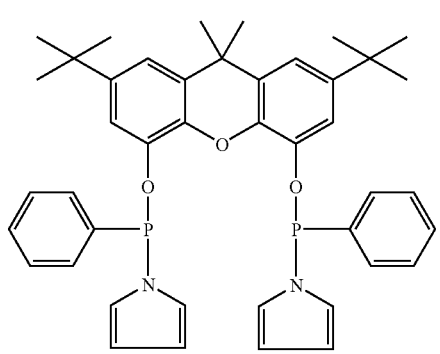
27
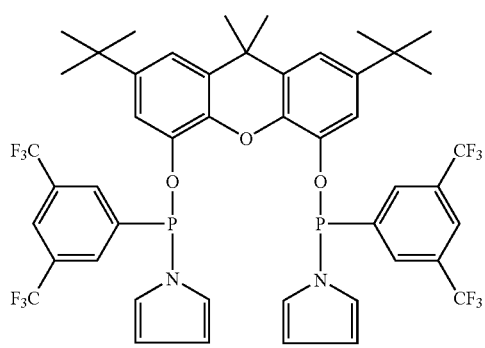
28
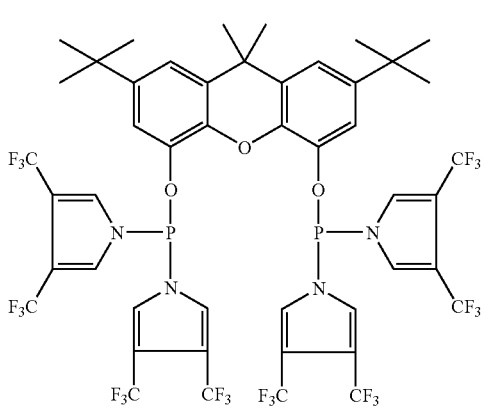
29
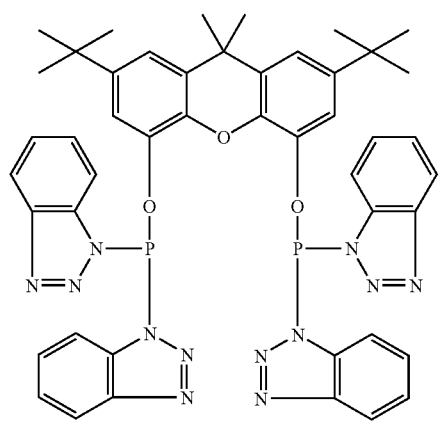
30
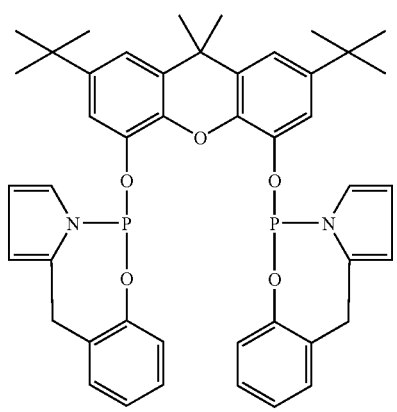
31
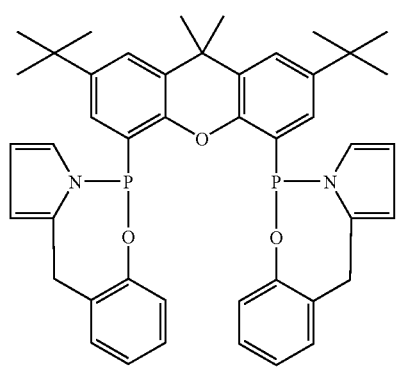
32
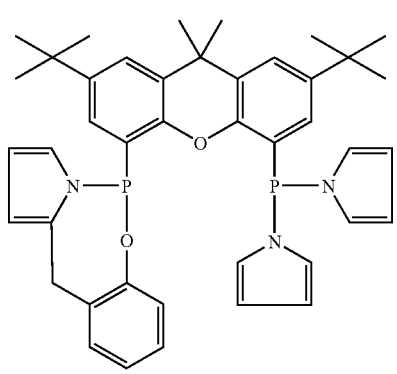

-continued
33
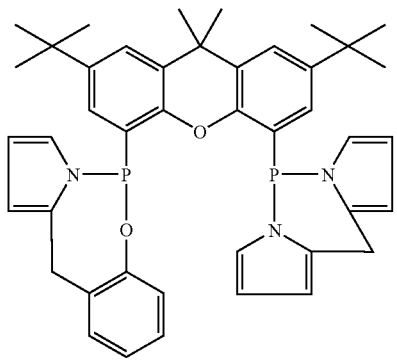
34
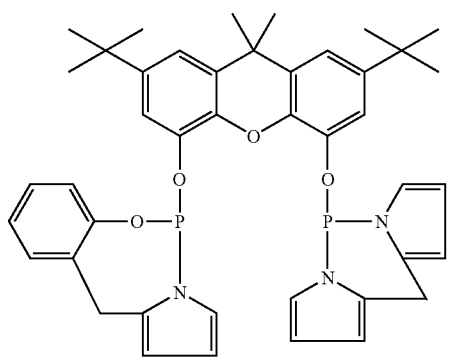
35
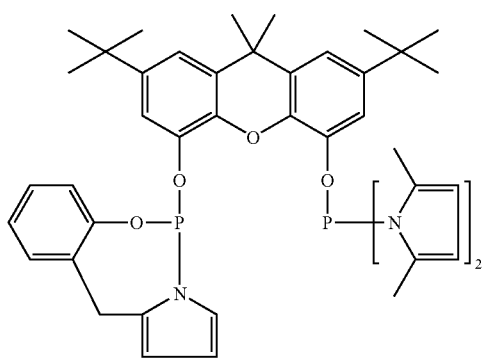
36
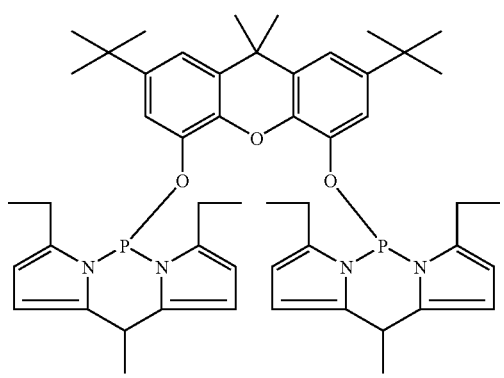
37
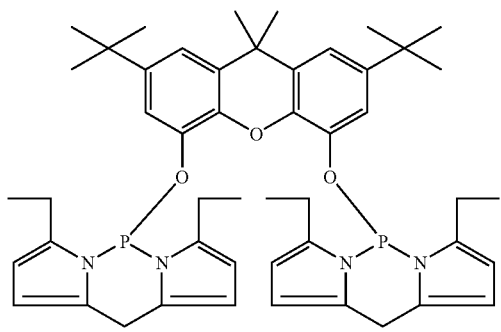
38
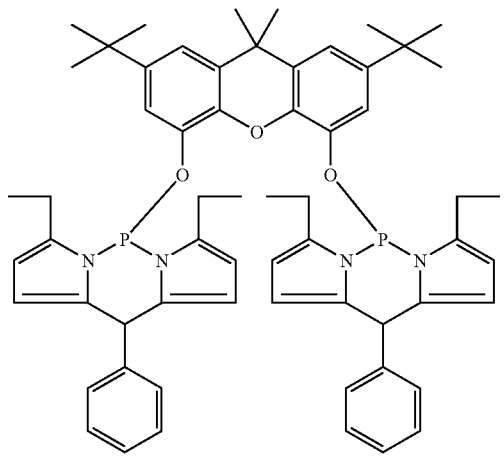
39
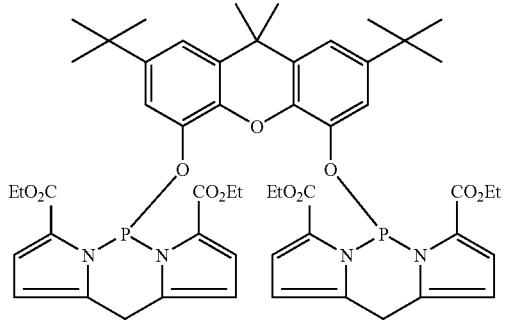
40
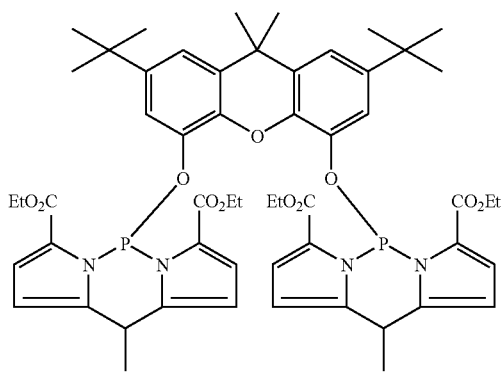

-continued
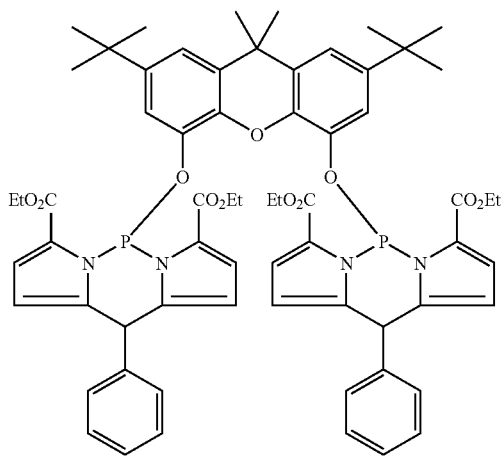
41
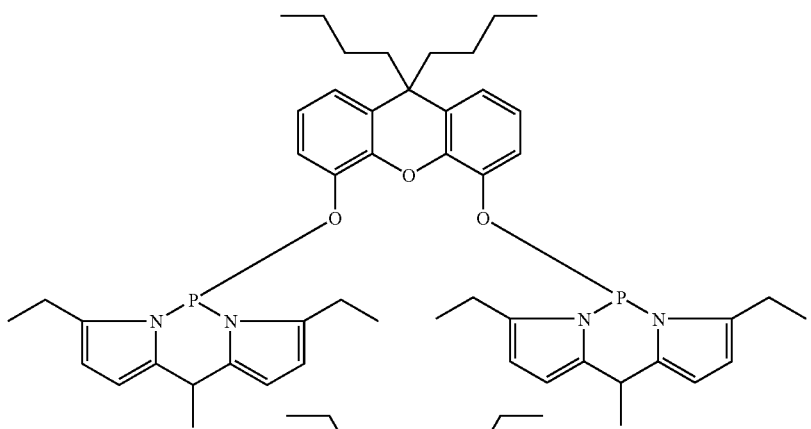
42
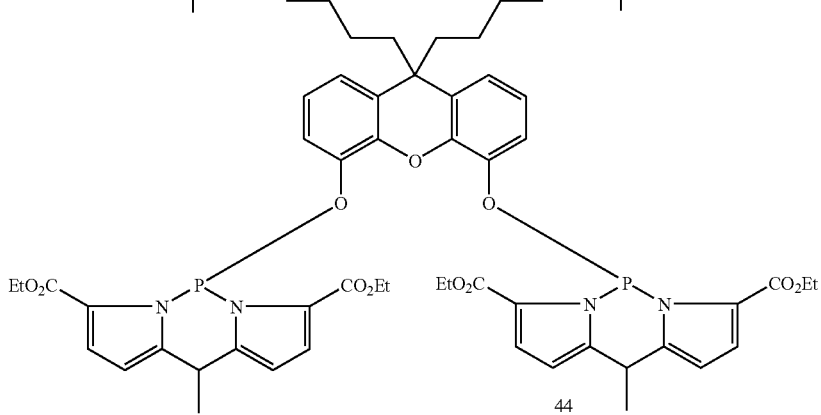
43
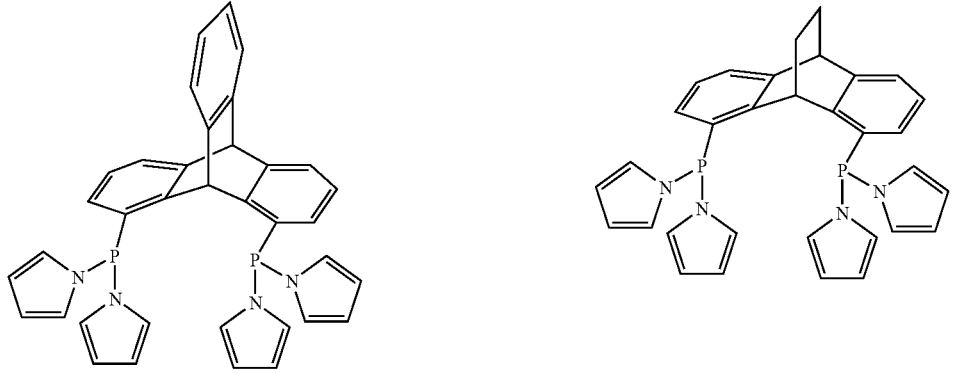
44    45

-continued
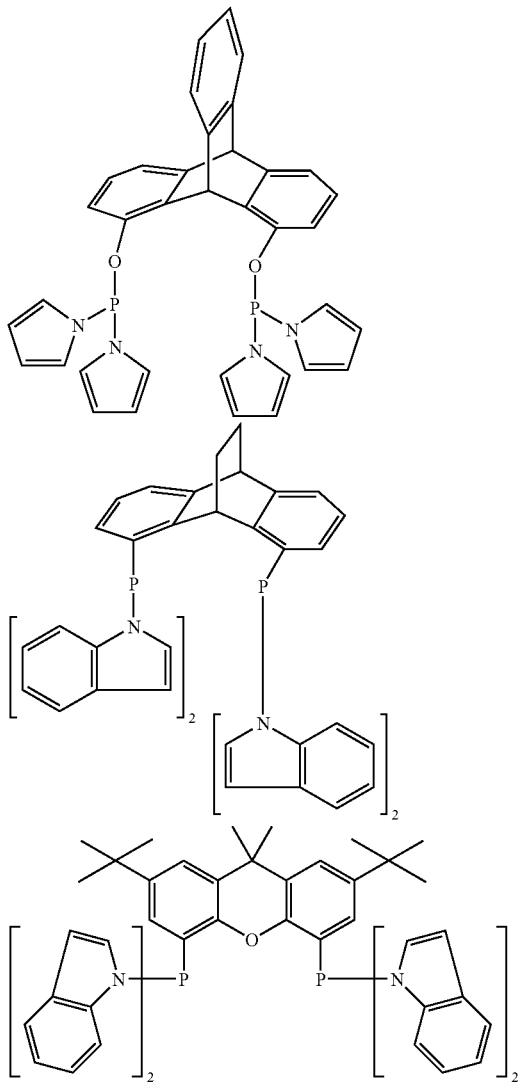
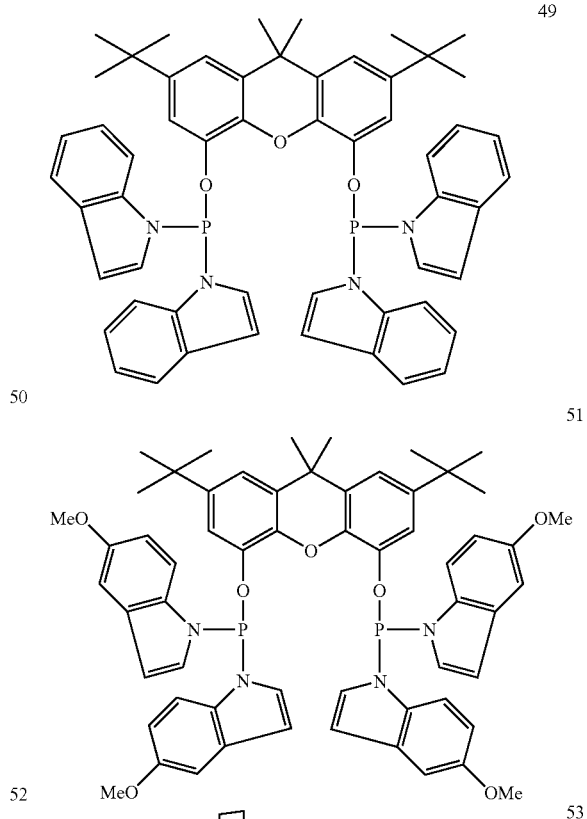

-continued

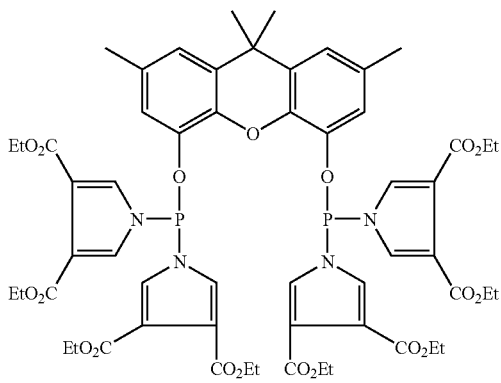

54

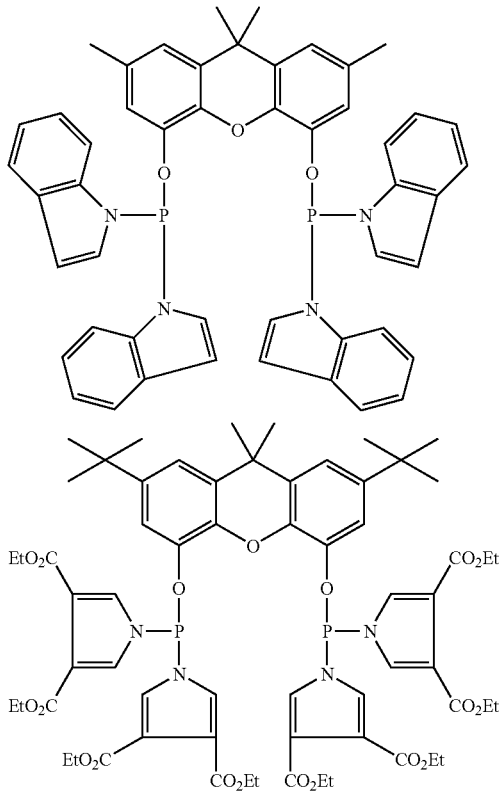

55

56

Me = methyl
Et = ethyl

The preparation of the chelating pnicogen compounds is described in WO 02/083695, which is hereby fully incorporated by reference.

In general, the catalysts or catalyst precursors used in each case are converted under hydroformylation conditions into catalytically active species of the formula $H_gZ_d(CO)_eG_f$, where Z is a metal of transition group VIII, G is a phosphorus-, arsenic- or antimony-containing ligand of the formula I or II and d, e, f, g are natural numbers which depend on the valence and type of the metal and on the number of coordination sites occupied by the ligand G. It is preferred that e and f each have, independently of one another, a value of at least 1, e.g. 1, 2 or 3. The sum of e and f is preferably from 2 to 5. If desired, the complexes of the metal Z with the ligands G used according to the present invention may further comprise at least one additional ligand which is not used according to the present invention, e.g. a ligand from the class of triarylphosphines, in particular triphenylphosphines, triaryl phosphites, triaryl phosphinites, triaryl phosphonites, phosphabenzenes, trialkylphosphines or phosphametallocenes. Such complexes of the metal Z with ligands used according to the invention and other ligands are formed, for example, in an equilibrium reaction after addition of a ligand to a complex of the formula $H_gZ_d(CO)_eG_f$.

In a preferred embodiment, the hydroformylation catalysts are prepared in situ in the reactor used for the hydroformylation reaction. However, the catalysts used in the process of the present invention can, if desired, also be prepared separately and isolated by customary methods. For the in-situ preparation of the catalysts, at least one compound of the formula I or II, a compound or a complex of a metal of transition group VIII, if desired one or more further ligands and, if desired, an activating agent can be reacted in an inert solvent under the hydroformylation conditions.

Suitable rhodium compounds or complexes are, for example, rhodium(II) and rhodium(III) salts such as rhodium(III) chloride, rhodium(III) nitrate, rhodium(III) sulfate, potassium rhodium sulfate, rhodium(II) and rhodium(III) carboxylate, rhodium(II) or rhodium(III) acetate, rhodium (III) oxide, salts of rhodic(III) acid, trisammonium hexachlororhodate(III), etc. Also suitable are rhodium complexes such as dicarbonylrhodium acetylacetonate, acetylacetonatobisethylenerhodium(I), etc. Preference is given to using dicarbonylrhodium acetylacetonate or rhodium acetate.

Likewise suitable are ruthenium salts or compounds. Suitable ruthenium salts are, for example, ruthenium(III) chloride, ruthenium(IV), ruthenium(VI) or ruthenium(VIII) oxide, alkali metal salts of ruthenium oxo acids such as $K_2RuO_4$ or $KRuO_4$ or complexes such as $RuHCl(CO)(PPh_3)_3$. It is also possible to use the carbonyls of ruthenium, for example dodecacarbonyltrisruthenium or octadecarbonylhexaruthenium, mixed forms in which CO is partly replaced by ligands of the formula $PR_3$, e.g. $Ru(CO)_3(PPh_3)_2$, in the process of the present invention.

Suitable cobalt compounds are, for example, cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate and cobalt naphthenoate. Here too, the carbonyl complexes of cobalt such as octacarbonyl dicobalt, dodecacarbonyl tetracobalt and hexadecacarbonyl hexacobalt can be used.

The abovementioned and further suitable compounds of cobalt, rhodium, ruthenium and iridium are known, are commercially available or their preparation is adequately described in the literature or they can be prepared by a person skilled in the art by methods analogous to those for the known compounds.

Suitable metals of transition group VIII are, in particular, cobalt and rhodium.

As solvents, preference is given to using the aldehydes formed in the hydroformylation of the respective olefins and also their higher-boiling downstream products, e.g. the products of the aldol condensation. Aromatics such as toluene and xylenes, hydrocarbons or mixtures of hydrocarbons are likewise suitable as solvents, including their use for dilution of the abovementioned aldehydes and the downstream products of the aldehydes. Further possible solvents are esters of aliphatic carboxylic acids with alkanols, for example ethyl acetate or Texanol®, ethers such as tert-butyl methyl ether and tetrahydrofuran. In the case of sufficiently hydrophilic ligands, it is also possible to use alcohols such as methanol, ethanol, n-propanol, isopropanol, n-butanol, isobutanol, ketones such as acetone and methyl ethyl ketone, etc. Furthermore, "ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl) phosphonium salts, e.g. the tetrafluoroborates, acetates, tetrachloroaluminates, hexafluorophosphates, chlorides and tosylates.

It is also possible to carry out the reactions in water or aqueous solvent systems comprising water together with a water-miscible solvent, for example an alcohol such as methanol, ethanol, n-propanol, isopropanol, n-butanol, isobutanol, a ketone such as acetone or methyl ethyl ketone or another solvent. For this purpose, use is made of ligands of the formula I or II which are modified with polar groups, for example ionic groups such as $SO_3M$, $CO_2M$ where M=Na, K or $NH_4$ or $N(CH_3)_4^+$. The reactions then occur as a two-phase catalysis with the catalyst being present in the aqueous phase and starting materials and products forming the organic phase. The reaction in the "ionic liquids" can also be carried out as a two-phase catalysis.

As substrates for the hydroformylation process of the present invention, it is in principle possible to use all compounds which contain at least two ethylenically unsaturated double bonds. These include, for example, dienes or polyenes having isolated or conjugated double bonds. Examples of suitable diolefins are compounds of the formula F,

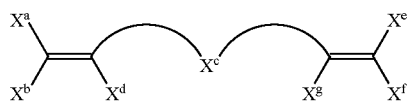

where
$X^a$, $X^b$, $X^d$ $X^e$, $X^f$, $X^g$ are each, independently of one another, hydrogen, alkyl, cycloalkyl, heterocycloalkyl, aryl, hetaryl, and $X^c$ is a single bond or $C_1$–$C_{20}$-alkanediyl which may bear one or more, for example 1, 2, 3, 4 or 5, substituents selected from the group consisting of cycloalkyl, aryl, hetaryl, halogen, $C_1$–$C_{20}$-alkoxy, $C_1$–$C_{20}$-alkoxycarbonyl and $NE^1E^2$ and/or may be interrupted by at least one further double bond and/or may be partly a constituent of one or more cycloalkyl groups, heterocycloalkyl groups, aryl groups or hetaryl groups, with the cycloalkyl groups and heterocycloalkyl groups also being able to be partially unsaturated.

The compound having at least two ethylenically unsaturated double bonds which is used for the hydroformylation is preferably selected from among diolefins having one terminal double bond and one internal double bond and α,ω-diolefins, i.e. diolefins having two terminal double bonds. α,ω-diolefins include, for example, 1,3-butadiene, 1,4-pentadiene, 1,5-hexadiene, 1,6-heptadiene, 1,7-octadiene, 1,8-nonadiene, 1,9-decadiene, 1,10-undecadiene, 1,11-dodecadiene, 1,12-tridecadiene, 1,13-tetradecadiene, 1,14-pentadecadiene, 1,15-hexadecadiene, 1,16-heptadecadiene, 1,17-octadecadiene, 1,18-nonadecadiene, 1,19-eicosadiene and mixtures thereof.

In the hydroformylation process of the present invention, preference is given to using an industrially available diolefin or diolefin mixture, preferably a mixture comprising α,ω-diolefins. Such mixtures include, for example, 1,3-butadiene-containing hydrocarbon mixtures. For example, the refining of petroleum by steam cracking of naphtha gives a hydrocarbon mixture known as $C_4$ fraction which has a high total olefin content, with about 20-60% by weight being 1,3-butadiene and the remainder being made up of monoolefins and multiply unsaturated hydrocarbons and alkanes. The 1,3-butadiene is separated off from these to give raffinates I. Pure 1,3-butadiene can generally be isolated from industrially available hydrocarbon mixtures by, for example, extractive distillation.

1,5-Hexadiene and 1,9-decadiene are prepared industrially by Shell. 1,7-Octadiene is obtained, for example, by reductive coupling of 1,3-butadiene in the presence of acetic acid and triethylamine as promoters.

Preference is given to a process in which the hydroformylation catalyst is prepared in situ by reacting at least one compound of the formula I or II, a compound or a complex of a metal of transition group VIII and, if appropriate, an activating agent in an inert solvent under the hydroformylation conditions. However, if desired, the ligand-metal complexes can also be prepared separately and be isolated by customary methods.

The hydroformylation reaction can be carried out continuously, semicontinuously or batchwise.

Suitable reactors for a continuous reaction are known to those skilled in the art and are described, for example, in Ullmanns Encyklopädie der technischen Chemie, Vol. 1, 3rd Edition, 1951, p. 743 ff.

Suitable pressure-rated reactors are likewise known to those skilled in the art and are described, for example, in Ullmanns Encyklopädie der technischen Chemie, Vol. 1, 3rd Edition, 1951, p. 769 ff. In general, the process of the present invention is carried out using an autoclave which may, if desired, be provided with a stirrer and an internal lining.

The composition of the synthesis gas comprising carbon monoxide and hydrogen used in the process of the present invention can vary within wide limits. The molar ratio of carbon monoxide to hydrogen is generally from about 5:95 to 70:30, preferably from about 40:60 to 60:40. Particular preference is given to using a molar ratio of carbon monoxide to hydrogen in the region of 1:1.

The temperature in the hydroformylation reaction is generally in a range from about 20 to 180° C., preferably from about 40 to 80° C., in particular from about 50 to 70° C. The reaction is generally carried out at the partial pressure of the reaction gas at the reaction temperature chosen. The pressure is generally in the range from about 1 to 700 bar, preferably from 1 to 600 bar, in particular from 1 to 300 bar. The reaction pressure can be varied as a function of the activity of the hydroformylation catalyst used. In general, the catalysts based on phosphorus-, arsenic- or antimony-containing chelating pnicogen compounds permit a reaction in a low pressure range, for instance in the range from 1 to 100 bar, preferably from 5 to 50 bar.

The molar ratio of chelating pnicogen compound I or II to the metal of transition group VIII in the hydroformylation medium is generally in the range from about 1:1 to 1000:1, preferably from 1:1 to 100:1, in particular from 1:1 to 50:1 and very particularly preferably from 1:1 to 20:1.

The molar ratio of metal of transition group VIII to substrate is usually below 1 mol %, preferably below 0.5 mol % and in particular below 0.1 mol % and very particularly preferably below 0.05 mol %.

The hydroformylation catalysts can be separated off from the reaction mixture obtained from the hydroformylation reaction by customary methods known to those skilled in the art and can generally be reused for the hydroformylation.

The above-described catalysts can also be immobilized in an appropriate manner, e.g. by bonding via functional groups suitable as anchor groups, by adsorption, by grafting, etc., on a suitable support, e.g. glass, silica gel, synthetic resins, etc. They are then also suitable for use as solid state catalysts.

It has been found that ethylenically unsaturated compounds, in particular those having at least one terminal double bond, can be hydroformylated advantageously at low temperatures and low pressures by means of the process of the present invention. This generally requires shorter reaction times and/or smaller amounts of catalyst system, based on substrate used, than would be necessary for hydroformylation of the same substrate using the same catalytically active metal but with other phosphorus-containing cocatalysts, e.g. xantphos (cf., for example, B. C. Botteghi et al. in J. Mol. Catal. A: Chem 2001, 175, 17, Table 2: high catalyst loading of 0.4–1 mol %). In particular, the process of the present invention makes it possible to carry out the hydroformylation of ethylenically unsaturated compounds, in particular those having two terminal,: double bonds, at reaction times of less than 15 hours, preferably less than 10 hours, using small amounts of catalyst system. An advantage is that no or very little isomerization of terminal double bonds to the thermodynamically stable internal double bonds takes place under the conditions of the hydroformylation using the catalysts employed according to the present invention. The catalysts used thus display a high n-selectivity, i.e. high yields of $\alpha,\omega$-enals and/or $\alpha,\omega$-dialdehydes are obtained from $\alpha,\omega$-diolefins.

One embodiment of the present invention relates to the preparation of dialdehydes. In a preferred variant, the preparation of the dialdehydes is carried out batchwise. Batch hydroformylation processes are known in principle to those skilled in the art. After the reaction is complete, the reactor is generally firstly depressurized. The synthesis gas thus liberated and any unreacted, unsaturated compounds can, if appropriate after work-up, be reused in full or in part. The remaining contents of the reactor consist essentially of dialdehyde, high-boiling by-products (hereinafter also referred to as high boilers) and catalyst. For the work-up, the contents of the reactor can be subjected to a single-stage or multistage fractionation to give at least one dialdehyde-enriched fraction. The fractionation to give a dialdehyde-enriched fraction can be carried out in various ways, for example by distillation, crystallization or membrane filtration, preferably by distillation. In a particularly preferred embodiment of the batch process, use is made of a reactor having a superposed distillation column, so that the product can be distilled directly from the reactor. The distillation column may, if desired, be provided with rectification trays to achieve very good separation performance. The distillation can be carried out at atmospheric pressure or under reduced pressure. The dialdehyde-enriched fraction can be isolated at the top or in the upper region of the column, while at least one dialdehyde-depleted fraction can be isolated at the bottom or in the lower region of the column. Suitable columns, temperature parameters and pressure parameters are known to those skilled in the art. The dialdehyde-enriched fraction can, if appropriate, be subjected to a further purification step. The dialdehyde-depleted fraction consists essentially of high boilers and the catalyst. The catalyst can be separated off by customary methods known to those skilled in the art and can generally, if appropriate after work-up, be reused in a further hydroformylation.

In a further preferred embodiment, the preparation of the dialdehydes is carried out continuously. In the continuous process, an unsaturated compound is subjected to hydroformylation in one or more reaction zones. An output is taken from the reaction zone and this is generally first depressurized. The depressurization liberates unreacted synthesis gas and unsaturated compounds which are generally, if appropriate after work-up, recirculated to the reaction zone. The fractionation of the remaining output to give a dialdehyde-enriched fraction can be carried out by means of customary measures known from the prior art, for example by distillation, crystallization or membrane filtration. Suitable distillation units are known to those skilled in the art. Furthermore, thin film evaporators, are also useful. In fractionation by distillation, a fraction consisting essentially of high boilers and catalyst is taken from the bottom or the lower region of the column and this can be recirculated directly to the reaction zone. However, preference is given to discharging all or part of the high boilers before recirculation and recirculating the catalyst, if appropriate after work-up, to the reaction zone. At least one dialdehyde-enriched fraction, which may further comprise unsaturated monoaldehyde, is taken off at the top or in the upper region of the column. The dialdehyde-enriched fraction which further comprises unsaturated monoaldehyde is advantageously subjected to at least one further fractionation in which at least one fraction enriched in unsaturated monoaldehyde and a fraction enriched in dialdehyde are obtained. The phase enriched in unsaturated monoaldehyde is recirculated to the reaction zone and the dialdehyde-enriched phase is discharged as product.

In a specific embodiment, the present invention provides a process for the hydroformylation of compounds having at least two ethylenically unsaturated double bonds with isolation of the unsaturated monoaldehydes (enals) formed.

The invention-therefore further provides a process which comprises (i) subjecting a compound having at least two ethylenically unsaturated double bonds to the hydroformylation reaction in a reaction zone, (ii) taking an output from the reaction zone and fractionating it to give a fraction enriched in unsaturated monoaldehydes and a fraction depleted in unsaturated monoaldehydes, and (iii) recirculating the fraction depleted in unsaturated monoaldehydes, if appropriate after work-up, to the reaction zone.

The process can be carried out either continuously, semi-continuously or batchwise. Preference is given to a continuous process.

In step (i) of the process of the present invention, the compound containing at least two ethylenically unsaturated double bonds is reacted with carbon monoxide and hydrogen in the presence of a hydroformylation catalyst comprising at least one complex of a metal of transition group VIII with at least one chelating pnicogen ligand of the formula I, as described above. As regards suitable and preferred hydroformylation catalysts and reaction conditions, reference may be made to what has been said above.

In step (ii), an output consisting essentially of unreacted multiply ethylenically unsaturated compounds, unsaturated monoaldehyde, dialdehyde and catalyst is taken from the reaction zone. The hydroformylation catalysts can be separated off by customary methods known to those skilled in the art and can generally be reused for the hydroformylation. The fractionation of the reaction mixture obtained in step (i) to give a fraction enriched in unsaturated monoaldehyde and a fraction depleted in unsaturated monoaldehyde can be carried out by means of measures known from the prior art (step ii). The fractionation is preferably carried out by distillation, by crystallization or by membrane filtration.

Suitable distillation units include all distillation apparatuses known to those skilled in the art for the continuous or batchwise fractionation of liquid mixtures. Furthermore, thin film evaporators are also useful. These include apparatuses in which the mixtures to be fractionated are distributed over heated surfaces by allowing them to trickle down (falling film evaporator, trickle column), with the aid of centrifugal force or by means of specially constructed wipers (wiped film evaporator, Sambay evaporator, filmtruder).

The output from the reaction zone is generally depressurized before being worked up by distillation. The unreacted synthesis gas and unreacted olefins liberated can be recirculated to the reaction zone. In the fractionation by distillation, the fraction enriched in unsaturated monoaldehydes is generally obtained as the top of the column. The fraction depleted in monoaldehydes which remains as bottom product can, if desired, be subjected to a further fractionation to give a catalyst-enriched fraction and a dialdehyde-enriched fraction. The dialdehyde-enriched fraction can, if desired, be discharged as further product of value.

The substrate recovered in the separation by distillation and the catalyst system are, in step (iii), recirculated to the reactor and once again subjected to hydroformylation.

The invention is illustrated by the following nonlimiting examples.

EXAMPLES

The following ligand was used:

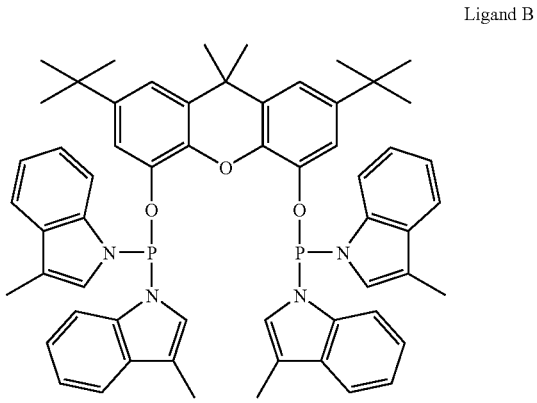

Ligand B

Example 1

Synthesis of ligand B 28.5 g (218 mmol) of 3-methylindole (skatole) together with about 50 ml of dry toluene were placed in a reaction vessel at room temperature and the solvent was distilled off under reduced pressure (removal of traces of water). This procedure was repeated once more. The residue was subsequently taken up in 700 ml of dry toluene under argon and cooled to −65° C. 14.9 g (109 mmol) of $PCl_3$ were then added at −65° C., followed by slow addition of 40 g (396 mmol) of triethylamine. The mixture was warmed to room temperature over a period of 16 hours and subsequently refluxed for 16 hours. 19.3 g (58 mmol) of 4,5-dihydroxy-2,7-di-tert-butyl-9,9-dimethylxanthene in 300 ml of dry toluene were then added at room temperature and the mixture was refluxed for 16 hours. The triethylamine hydrochloride formed was filtered off and washed once with toluene. After evaporation of the organic phases, the residue was recrystallized twice from hot ethanol. Drying under reduced pressure gave 36.3 g (71% of theory) of a colorless solid.

$^{31}P$-NMR (298 K) δ: 105 ppm.

Example 2

Hydroformylation of 1,7-octadiene using ligand B 5.0 mg of $Rh(CO)_2$acac (acac=acetylacetonate) and 181 mg of ligand B (99 ppm of Rh=0.02 mol %, ligand:Rh=10:1) were weighed out separately, each dissolved in 5 g of toluene, mixed and treated with 10 bar of synthesis gas ($CO:H_2$=1:1) at 60° C. After 30 minutes, the autoclave was depressurized, 10 g of 1,7-octadiene were then added, 20 bar of synthesis gas ($CO:H_2$=1:1) were injected and the mixture was hydroformylated at 60° C. for 6 hours. The conversion was 98%, the dial selectivity was 84% and the linearity was 98% (both double bonds hydroformylated terminally). The 1,10-decanedial was subsequently distilled at 69–71° C./1 mbar (not calibrated).

GC/MS (ionization:EI):molecular peak 170.

$^1$H-NMR (CDCl$_3$, 400 MHz, 298K):δ=1.05 (broad s, C4, C4', C5, C5', 8H), 1.35 (quintet, J=7 Hz, C3, C3', 4H), 2.17 (dt, J=1.7 Hz and 7.3 Hz, C2, C2', 4H), 9.47 (t, J=1.7 Hz, C1, C1', 2H).

$^{13}$C{$^1$H}-NMR (CDCl$_3$, 101 MHz, 298K) [DEPT-135]: δ=22.1 (C5, C5', [CH$_2$]), 29.2 (C4, C4', [CH$_2$]), 29.3 (C3, C3', [CH$_2$]), 43.9 (C2, C2', [CH$_2$]), 202.4 (C1, C1', [CH, CH$_3$]).

Example 3

Hydroformylation of 1,7-octadiene 5.0 mg of Rh(CO)$_2$acac and 181 mg of ligand B (99 ppm of Rh=0.02 mol %, ligand: Rh=10:1) were weighed out separately, each dissolved in 5 g of toluene, mixed and treated with 10 bar of synthesis gas (CO:H$_2$=1:1) at 80° C. After 30 minutes, the autoclave was depressurized, 10 g of 1,7-octadiene were then added, 20 bar of synthesis gas (CO:H$_2$=1:1) were injected and the mixture was hydroformylated at 80° C. for 6 hours. The conversion was 99%, the dial selectivity was 34% and the linearity was 96% (both double bonds hydroformylated terminally).

Example 4

Hydroformylation of 1,9-decadiene 5.1 mg of Rh(CO)$_2$acac and 202 mg of ligand B (100 ppm of Rh=0.03 mol %, ligand: Rh=11:1) were weighed out separately, each dissolved in 5 g of toluene, mixed and treated with 10 bar of synthesis gas (CO:H$_2$=1:1) at 100° C. After 30 minutes, the mixture was cooled to 60° C., depressurized, and 10 g of 1,9-decadiene were then added, 20 bar of synthesis gas (CO:H$_2$=1:1) were injected and the mixture was hydroformylated at 60° C. for 8 hours. The conversion was 97%, the dial selectivity was 92% and the linearity was 98% (both double bonds hydroformylated terminally). The 1,12-dodecanedial obtained was subsequently distilled at 130–140° C./7–10 mbar (not calibrated).

GC/MS (ionization: EI): molecular peak 198.

$^1$H-NMR (CDCl$_3$, 400 MHz, 298K):δ=1.06 (broad s, C4, C4', C5, C5', C6, C6', 12H), 1.38 (quintet, J=7.1 Hz, C3, C3', 4H), 2.18 (dt, J=1.7 Hz and 7.3 Hz, C2, C2', 4H), 9.50 (t, J=1.7 Hz, C1, C1', 2H).

$^{13}$C{$^1$H}-NMR (CDCl$_3$, 101 MHz, 298K) [DEPT-135] δ=22.18 (C6, C6', [CH$_2$]), 29.27 (C5, C5', [CH$_2$]), 29.47 (C4, C4', [CH$_2$]), 29.48 (C3, C3', [CH$_2$]), 43.92 (C2, C2', [CH$_2$]), 202.41 (C1, C1', [CH, CH$_3$]).

Example 5

Reaction kinetics: formation of undec-10-en-1-al in the hydroformylation of 1,9-decadiene 5.1 mg of Rh(CO)$_2$acac and 202 mg of ligand B (100 ppm of Rh, ligand: Rh=11:1) were weighed out separately, each dissolved in 5 g of toluene, mixed and treated with 10 bar of synthesis gas (CO:H$_2$=1:1) at 100° C. After 30 minutes, the mixture was cooled to 60° C., depressurized, and 10 g of 1,9-decadiene were then added, 20 bar of synthesis gas (CO:H$_2$=1:1) were injected and the mixture was hydroformylated at 60° C. Samples were taken after various times and analyzed. The intermediate was additionally identified by GC-MS. FIG. 1 shows a graphical presentation of Example 5.

The invention claimed is:

1. A process for preparing dialdehydes and/or ethylenically unsaturated monoaldehydes by reacting at least one compound having at least two ethylenically unsaturated double bonds with carbon monoxide and hydrogen in the presence of a hydroformylation catalyst comprising at least one complex of a metal of transition group VIII with at least one ligand selected from among chelating pnicogen compounds of the formula I,

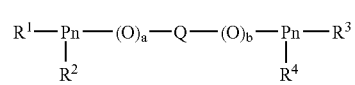

where
Q is a bridging group of the formula

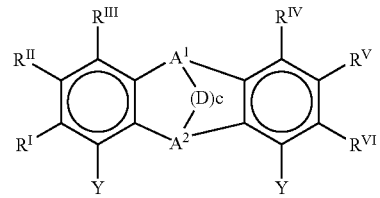

where
A$^1$ and A$^2$ are each, independently of one another, O, S, SiR$^a$R$^b$, NR$^c$ or CR$^d$R$^e$, where
R$^a$, R$^b$ and R$^c$ are each, independently of one another, hydrogen, alkyl, cycloalkyl, heterocycloalkyl, aryl or hetaryl,
R$^d$ and R$^e$ are each, independently of one another, hydrogen, alkyl, cycloalkyl, heterocycloalkyl, aryl or hetaryl or the group R$^d$ together with a further group R$^d$ or the group R$^e$ together with a further group R$^e$ form an intramolecular bridging group D,
D is a divalent bridging group selected from among the groups

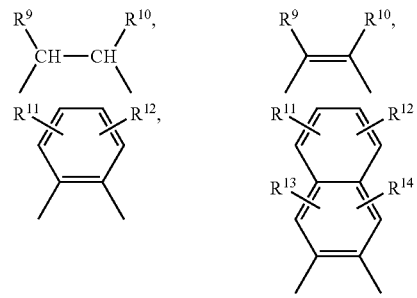

where
R$^9$ and R$^{10}$ are each, independently of one another, hydrogen, alkyl, cycloalkyl, aryl, halogen, trifluoromethyl, carboxyl, carboxylate or cyano or are joined to one another to form a C$_3$–C$_4$-alkylene bridge,
R$^{11}$, R$^{12}$, R$^{13}$ and R$^{14}$ are each, independently of one another, hydrogen, alkyl, cycloalkyl, aryl, halogen, trifluoromethyl, COOH, carboxylate, cyano, alkoxy, SO$^3$H, sulfonate, NE$^1$E$^2$, alkylene-NE$^1$E$^2$E$^{3+}$X$^-$, acyl or nitro,
c 0 or 1,
Y is a chemical bond, $R^I$, $R^{II}$, $R^{III}$, $R^{IV}$, $R^V$ and $R^{VI}$ are each, independently of one another, hydrogen, alkyl, cycloalkyl, heterocycloalkyl, aryl, hetaryl, $COOR^f$, $COO^-M^+$, $SO_3R^f$, $SO_3^-M^+$, $NE^1E^2$, $NE^1E^2E^{3+}X^-$, alkylene-$NE^1E^2E^{3+}X^-$, $OR^f$, $SR^f$, $(CHR^gCH_2O)_xR^f$, $(CH_2N(E^1))_xR^f$, $(CH_2CH_2N(E^1))_xR^f$, halogen, trifluoromethyl, nitro, acyl or cyano, where
$R^f$, $E^1$, $E^2$ and $E^3$ are identical or different radicals selected from among hydrogen, alkyl, cycloalkyl and aryl,
$R^g$ is hydrogen, methyl or ethyl,
$M^+$ is a cation,
$X^-$ is an anion, and
x is an integer from 1 to 120, or
two adjacent radicals selected from among $R^I$, $R^{II}$, $R^{III}$, $R^{IV}$, $R^V$ and $R^{VI}$ together with two adjacent carbon atoms of the benzene ring to which they are bound for a fused ring system having 1, 2 or 3 further rings,
a and b are each, independently of one another, 0 or 1,
Pn is a pnicogen atom selected from among the elements phosphorus, arsenic and antimony,
and
$R^1$, $R^2$, $R^3$, $R^4$ are each, independently of one another, hetaryl, hetaryloxy, alkyl, alkoxy, aryl, aryloxy, cycloalkyl, cycloalkoxy, heterocycloalkyl, heterocycloalkoxy or an $NE^1E^2$ group, with the proviso that $R^1$ and $R^3$ are pyrrole groups bound via the nitrogen atom to the pnicogen atom Pn
or $R^1$ together with $R^2$ and/or $R^3$ together with $R^4$ form a divalent group E of the formula Py—I—W where
Py is a pyrrole group which is bound via the pyrrole nitrogen atom to the pnicogen atom Pn,
I is a chemical bond or O, S, $SiR^aR^b$, $NR^c$, substituted or unsubstituted $C_1$–$C_{10}$-alkylene or $CR^hR^i$,
W is cycloalkyl, cyoloalkoxy, aryl, aryloxy, hetaryl or hetaryloxy,
and
$R^h$ and $R^i$ are each, independently of one another, hydrogen, alkyl, cycloalkyl, heterocycloalkyl, aryl or hetaryl,
or $R^1$ together with $R^2$ and/or $R^3$ together with $R^4$ form a bispyrrole group of the formula Py—I—Py bound via the nitrogen atoms to the pnicogen atom Pn.

2. A process as claimed in claim 1, wherein at least one ligand of the formula I, in which the radicals $R^1$, $R^2$, $R^3$ and $R^4$ are selected independently from among groups of the formulae I.a to I.k

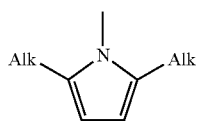 (I.a)

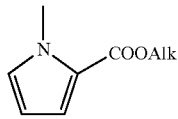 (I.b)

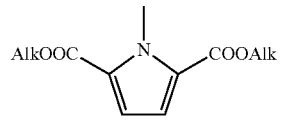 (I.c)

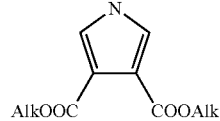 (I.d)

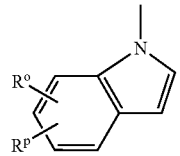 (I.e)

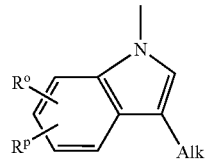 (I.f)

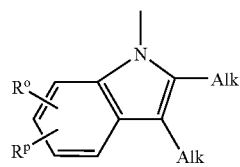 (I.g)

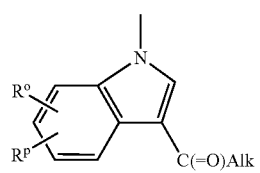 (I.h)

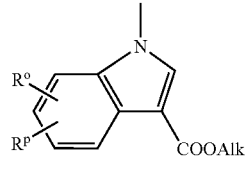 (I.i)

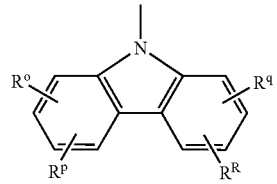 (I.k)

where
Alk is a $C_1$–$C_4$-alkyl group and
$R^o$, $R^p$, $R^q$ and $R^r$ are each, independently of one another, hydrogen, $C_1$–$C_4$-alkyl, $C_1$–$C_4$-alkoxy, acyl, halogen, trifluoromethyl, $C_1$–$C_4$-alkoxycarbonyl or carboxyl, is used.

3. A process as claimed in claim 2, wherein at least one ligand of the formula I, in which the radicals $R^1$, $R^2$, $R^3$ and $R^4$ are each, independently of one another, a 3-alkylindolyl group is used.

4. A process as claimed in claim 1, wherein the chelating pnicogen compound of the formula I is selected from among chelating pnicogen compounds of the formula II,

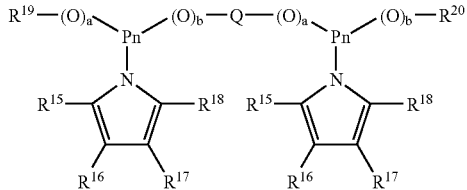

(II)

where $R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^1$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CHR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, where W' is a single bond, a heteroatom or a divalent bridging group having from 1 to 20 bridge atoms, R$^k$, E$^4$, E$^5$, E$^6$ are identical or different radicals selected from among hydrogen, alkyl, cycloalkyl and aryl, R$^1$ is hydrogen, methyl or ethyl, M$^+$ is a cation equivalent, X$^-$ is an anion equivalent and y is an integer from 1 to 240, where two adjacent radicals $R^{15}$, $R^{16}$, $R^{17}$ and $R^{18}$ together with the carbon atoms of the pyrrole ring to which they are bound may also form a fused ring system having 1, 2 or 3 further rings, with the proviso that at least one of the radicals $R^{15}$, $R^{16}$, $R^{17}$ and $R^{18}$ is not hydrogen and $R^{19}$ and $R^{20}$ are not joined to one another, $R^{19}$ and $R^{20}$ are each, independently of one another, cycloalkyl, heterocycloalkyl, aryl or hetaryl, or $R^{19}$ together with $R^{15}$ or $R^{16}$ and/or $R^{19}$ together with $R^{17}$ or $R^{18}$ form a divalent group

—I—W— where

I is a chemical bond or O, S, SiR$^a$R$^b$, NR$^c$ or substituted or unsubstituted C$_1$–C$_{10}$-alkylene, preferably CR$^h$Ri, where R$^a$, R$^b$, R$^c$, R$^h$ and R$^i$ are each, independently of one another, hydrogen, alkyl, cycloalkyl, heterocycloalkyl, aryl or hetaryl and W is cycloalkyl, cycloalkoxy, aryl, aryloxy, hetaryl or hetaryloxy.

5. A process as claimed in claim 1, wherein the chelating pnicogen compound of the formula I is a chelating pnicogen compound of the formulae II.1 to II.3,

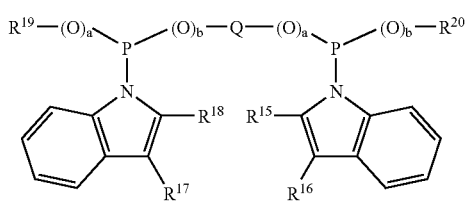

(II.1)

-continued

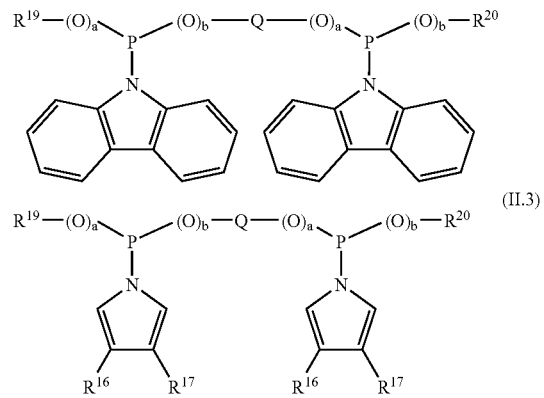

(II.2)

(II.3)

where

Q, a and b are as defined in claim 1, $R^{15}$, $R^{16}$, $R^{17}$ and $R^{18}$ are each, independently of one another, hydrogen, alkyl, cycloalkyl, heterocycloalkyl, aryl, hetaryl, W'COOR$^k$, W'COO$^-$M$^+$, W'(SO$_3$)R$^k$, W'(SO$_3$)$^-$M$^+$, W'PO$_3$(R$^k$)(R$^1$), W'(PO$_3$)$^{2-}$(M$^+$)$_2$, W'NE$^4$E$^5$, W'(NE$^4$E$^5$E$^6$)$^+$X$^-$, W'OR$^k$, W'SR$^k$, (CNR$^1$CH$_2$O)$_y$R$^k$, (CH$_2$NE$^4$)$_y$R$^k$, (CH$_2$CH$_2$NE$^4$)$_y$R$^k$, halogen, trifluoromethyl, nitro, acyl or cyano, wherein W' is a single bond, a heteroatom or a divalent bridging group having from 1 to 20 bridge atoms, R$^k$, E$^4$, E$^5$, E$^6$ are identical or different radicals selected from among hydrogen, alkyl, cycloalkyl and aryl, R$^1$ is hydrogen, methyl or ethyl, M$^+$ is a cation equivalent, X$^-$ is an anion equivalent and y is an integer from 1 to 240, where two adjacent radicals $R^{15}$, $R^{16}$, $R^{17}$ and $R^{18}$ together with the carbon atoms of the pyrrole ring to which they are bound may also form a fused ring system having 1, 2 or 3 further rings, where at least one of the radicals $R^{16}$ and $R^{17}$ in the formula II.3 is not hydrogen, $R^{19}$ and $R^{20}$ are each, independently of one another, cycloalkyl, heterocycloalkyl, aryl or hetaryl.

6. A process as claimed in claim 1, wherein the bridging group Q is a triptycenediyl group of the formula

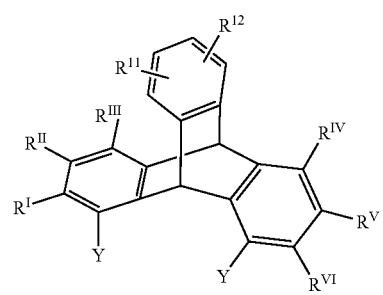

or the formula

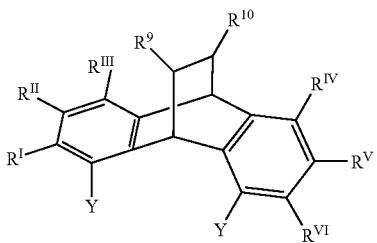

where $R^I$, $R^{II}$, $R^{III}$, $R^{IV}$, $R^V$ and $R^{VI}$, $R^9$, $R^{10}$, $R^{11}$ and $R^{12}$ are as defined in claim 1.

7. A process as claimed in claim 1, wherein the bridging group Q is a xanthenediyl group of the formula

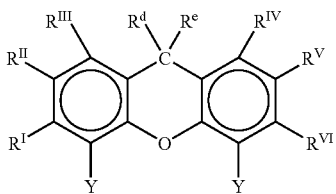

where $R^I$, $R^{II}$, $R^{III}$, $R^{IV}$, RV and $R^{VI}$ and Y are as defined in claim 1 and $R^d$ and $R^e$ are each, independently of one another, hydrogen, alkyl, cycloalkyl, heterocyloalkyl, aryl or hetaryl.

8. A process as claimed in claim 1, wherein a molar ratio of ligand to metal of transition group VIII of from 1:1 to 1000:1 is set in the reaction mixture.

9. A process as claimed in claim 1, wherein the reaction is carried out at from 40 to 80° C.

10. A process as claimed in claim 1, wherein the compound having at least two ethylenically unsaturated double bonds which is used is a a,w-diolefin.

11. A process as claimed in claim 1, wherein
  (i) a compound having a least two ethylenically unsaturated double bonds is subjected to the hydroformylation reaction in a reaction zone,
  (ii) an output is taken from the reaction zone and is fractionated to give a fraction enriched in unsaturated monoaldehydes and a fraction depleted in unsaturated monoaldehydes, and
  (iii) the fraction depleted in unsaturated monoaldehydes is recirculated, optionally after work up, to the reaction zone.

12. A process as claimed in claim 2, wherein at least one ligand of the formula I, in which the radicals $R^1$, $R^2$, $R^3$ and $R^4$ are each, independently of one another, a 3-methylindolyl group.

* * * * *

UNITED STATES PATENT AND TRADEMARK OFFICE
CERTIFICATE OF CORRECTION

PATENT NO.        : 7,145,042 B2
APPLICATION NO.   : 10/527635
DATED             : December 5, 2006
INVENTOR(S)       : Martin Volland et al.

It is certified that error appears in the above-identified patent and that said Letters Patent is hereby corrected as shown below:

Title Page 2, column 2 Item (56), References Cited, Other Publications, Benincori et al., should cite pp. 8340 - 8347.

In Claim 1, column 2, line 64 "$SO^3H$, sulfonate, $NE^1E^2$, alkylene-$NE^1E^2E^{3+}X^-$, acyl" should read -- $SO_3H$, sulfonate, $NE^1E^2$, alkylene-$NE^1E^2E^{3+}X^-$, acyl --.

In Claim 1, column 43, line 3, "cloalkyl, aryl, hetaryl, $COOR^f$, $COO-M^+, SO_3R^f$," should read -- cloalkyl, aryl, hetaryl, $COOR^f$, $COO^-M^+$, $SO_3R^f$, --.

In Claim 1, column 43, line 4, "$SO-_3M^+$, $NE^1E^2$, $NE^1E^2E^{3+}X^-$, alkylene-$NE^1E^2E^{3+}$" should read --$SO^-_3M^+$, $NE^1E^2$, $NE^1E^2E^{3+}X^-$, alkylene-$NE^1E^2E^{3+}$--.

In Claim 2, column 44, lines 50-55, Formula (I,k)

"
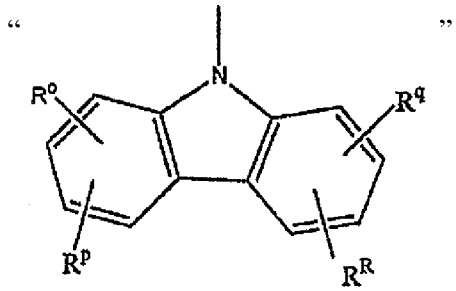
"

UNITED STATES PATENT AND TRADEMARK OFFICE
CERTIFICATE OF CORRECTION

PATENT NO.      : 7,145,042 B2
APPLICATION NO. : 10/527635
DATED           : December 5, 2006
INVENTOR(S)     : Martin Volland et al.

It is certified that error appears in the above-identified patent and that said Letters Patent is hereby corrected as shown below:

In Claim 2, column 44, lines 50-55, Formula (I,k) (cont'd)

should be

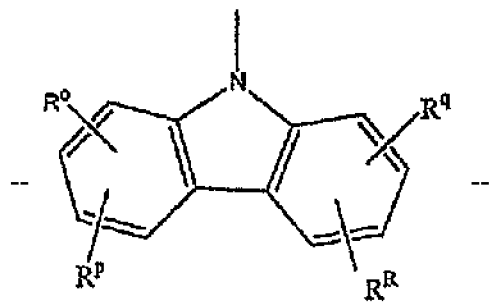

Signed and Sealed this

Fifteenth Day of May, 2007

JON W. DUDAS
*Director of the United States Patent and Trademark Office*

UNITED STATES PATENT AND TRADEMARK OFFICE
CERTIFICATE OF CORRECTION

PATENT NO. : 7,145,042 B2
APPLICATION NO. : 10/527635
DATED : December 5, 2006
INVENTOR(S) : Martin Volland et al.

It is certified that error appears in the above-identified patent and that said Letters Patent is hereby corrected as shown below:

Title Page 2, column 2 Item (56), References Cited, Other Publications, Benincori et al., should cite pp. 8340 - 8347.

In Claim 1, column 2, line 64 "$SO^3H$, sulfonate, $NE^1E^2$, alkylene-$NE^1E^2E^{3+}X^-$, acyl" should read -- $SO_3H$, sulfonate, $NE^1E^2$, alkylene-$NE^1E^2E^{3+}X^-$, acyl --.

In Claim 1, column 43, line 3, "cloalkyl, aryl, hetaryl, $COOR^f$, COO—$M^+$,$SO_3R^f$," should read -- cloalkyl, aryl, hetaryl, $COOR^f$, $COO^-M^+$, $SO_3R^f$, --.

In Claim 1, column 43, line 4, "SO—$_3M^+$, $NE^1E^2$, $NE^1E^2E^{3+}X^-$, alkylene-$NE^1E^2E^{3+}$" should read --$SO^-_3M^+$, $NE^1E^2$, $NE^1E^2E^{3+}X^-$, alkylene-$NE^1E^2E^{3+}$--.

In Claim 2, column 44, lines 50-55, Formula (I,k)

"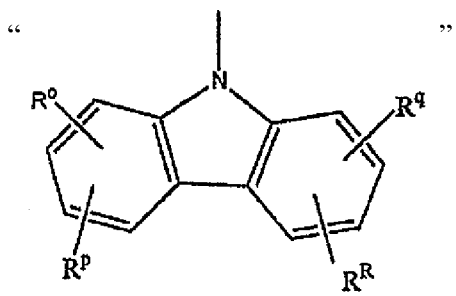"

UNITED STATES PATENT AND TRADEMARK OFFICE
CERTIFICATE OF CORRECTION

PATENT NO. : 7,145,042 B2
APPLICATION NO. : 10/527635
DATED : December 5, 2006
INVENTOR(S) : Martin Volland et al.

It is certified that error appears in the above-identified patent and that said Letters Patent is hereby corrected as shown below:

In Claim 2, column 44, lines 50-55, Formula (I,k) (cont'd)

should be

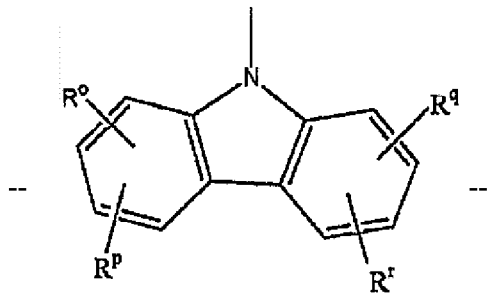

This certificate supersedes Certificate of Correction issued May 15, 2007.

Signed and Sealed this

Fourteenth Day of August, 2007

JON W. DUDAS
*Director of the United States Patent and Trademark Office*